(12) United States Patent
Fankhauser et al.

(10) Patent No.: US 6,495,122 B2
(45) Date of Patent: Dec. 17, 2002

(54) USE OF MIXTURES OF MICROPIGMENTS FOR PREVENTING TANNING AND FOR LIGHTENING SKIN AND HAIR

(75) Inventors: Peter Fankhauser, Ettingen (CH); Helmut Luther, Grenzach-Wyhlen (DE); Werner Baschong, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/067,027

(22) Filed: Feb. 4, 2002

(65) Prior Publication Data

US 2002/0155073 A1 Oct. 24, 2002

Related U.S. Application Data

(63) Continuation of application No. 09/612,748, filed on Jul. 10, 2000.

(30) Foreign Application Priority Data

Jul. 12, 1999 (CH) ............................................. 1281/99

(51) Int. Cl.[7] ............................ A61K 7/40; A61K 7/44; A61K 7/06; A61K 7/00
(52) U.S. Cl. .......................... 424/59; 424/60; 424/70.9; 424/401
(58) Field of Search ............................ 424/59, 60, 70.9, 424/401

(56) References Cited

U.S. PATENT DOCUMENTS

| | | | |
|---|---|---|---|
| 5,869,030 A | 2/1999 | Dümler et al. | 424/59 |
| 5,955,060 A | 9/1999 | Hüglin et al. | 424/59 |
| 5,980,872 A | 11/1999 | Luther et al. | 424/59 |
| 6,180,090 B1 | 1/2001 | Gers-Barlag et al. | 424/59 |
| 6,217,856 B1 | 4/2001 | Ehlis et al. | 424/70.9 |
| 6,221,342 B1 | 4/2001 | Hüglin et al. | 424/59 |
| 6,235,271 B1 | 5/2001 | Luther et al. | 424/59 |

FOREIGN PATENT DOCUMENTS

GB  2303549  2/1997

*Primary Examiner*—Shelley A. Dodson
(74) *Attorney, Agent, or Firm*—Kevin T. Mansfield

(57) ABSTRACT

The invention describes the use of micronized organic UV filters for preventing tanning and for lightening human skin and hair, and their use in cosmetic and pharmaceutical formulations.

The micronized UV filters used according to the invention cover a broad UV spectrum and therefore have excellent sunscreen properties.

31 Claims, No Drawings

USE OF MIXTURES OF MICROPIGMENTS FOR PREVENTING TANNING AND FOR LIGHTENING SKIN AND HAIR

This is a continuation of application Ser. No. 09/612,748, filed on Jul. 10, 2000.

The present invention relates to the use of mixtures of micronized organic UV filters for preventing tanning and for lightening human skin and hair and to their use in cosmetic and pharmaceutical formulations.

It is known that certain organic UV filters, for example sparingly soluble benzotriazole or triazine compounds, have excellent UV filter properties if they are in micronized form.

Particularly in Asiatic countries, there is great interest in light protection filters or mixtures of light protection filters which preserve the colour of the skin following solar irradiation and, moreover, are able to impart a lighter appearance to the skin.

The object of the present invention is therefore to find micronized organic UV filters which prevent tanning of the skin and at the same time are able to lighten the skin.

Surprisingly, we have now found that micronized organic UV filters or mixtures of at least two micronized UV filters can achieve this object.

The present invention therefore provides for the use of mixtures of micronized organic UV filters for preventing tanning and for lightening of human skin.

Suitable UV filters which can be used according to the invention are organic, sometimes sparingly soluble, compounds, for example triazine derivatives, in particular hydroxyphenyltriazine compounds or benzotriazole derivatives, amides containing a vinyl group, cinnamic acid derivatives, sulfonated benzimidazoles, Fischer base derivatives, diphenylmalonitriles, oxalylamides, camphor derivatives, diphenylacrylates, paraaminobenzoic acid (PABA) and derivatives thereof, salicylates, benzophenones and also other classes of substance known as UV filters.

Preferred triazine derivatives which can be used according to the invention correspond to the formula

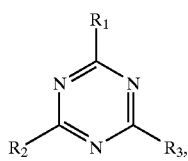
(1)

in which

R$_1$, R$_2$ and R$_3$, independently of one another, are hydrogen; OH; C$_1$–C$_{18}$alkoxy; —NH$_2$; —NH—R$_4$; —N(R$_4$)$_2$; —OR$_4$, R$_4$ is C$_1$–C$_5$alkyl; phenyl, phenoxy, anilino or pyrrolo which are unsubstituted or substituted by one, two or three OH groups, carboxyl, —CO—NH$_2$, C$_1$–C$_5$alkyl or C$_1$–C$_5$alkoxy; a methylidenecamphor group; a group of the formula —(CH=CH)$_m$C(=O)—OR$_4$; a group of the formula

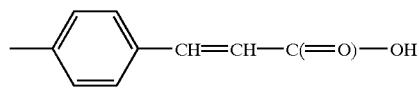

or the corresponding alkali metal, ammonium, mono-, di- or tri-C$_1$–C$_4$alkylammonium, mono-, di- or tri-C$_2$–C$_4$alkanolammonium salts, or C$_1$–C$_3$alkyl esters thereof; or a radical of the formula (1a)

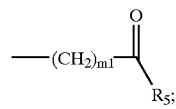

R$_5$ is hydrogen; unsubstituted C$_1$–C$_5$alkyl or C$_1$–C$_5$alkyl substituted by one or more OH groups; C$_1$–C$_5$alkoxy; amino; mono- or di-C$_1$–C$_5$alkylamino; M; a radical of the formula

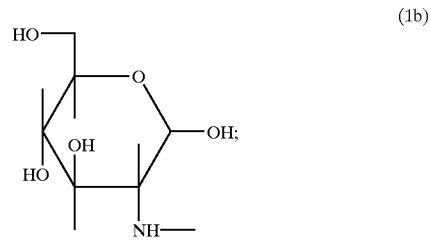
(1b)

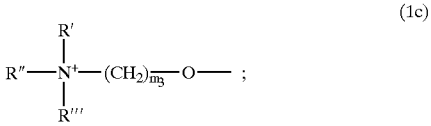
(1c)

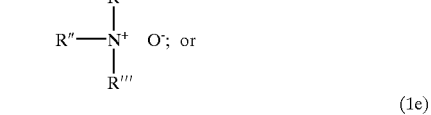
(1d)

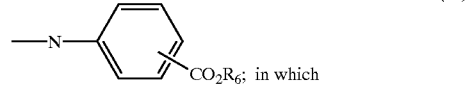
(1e)

R', R'' and R''', independently of one another, are unsubstituted C$_1$–C$_{14}$alkyl or C$_1$–C$_{14}$alkyl substituted by one or more OH groups;

R$_6$ is hydrogen; M; C$_1$–C$_5$alkyl; or a radical of the formula —(CH$_2$)$_{m_2}$—O—T$_1$;

M is a metal cation;

T$_1$ is hydrogen; or C$_1$–C$_8$alkyl;

m is 0 or 1 m$_2$ is 1 to 4; and m$_3$ is 2 to 14.

Further preferred triazine derivatives which can be used according to the invention correspond to the formula

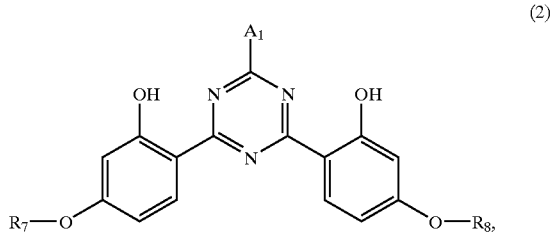
(2)

in which

R$_7$ and R$_8$, independently of one another, are C$_1$–C$_{18}$alkyl; C$_2$–C$_{18}$alkenyl; a radical of the formula —CH$_2$—CH(—OH)—CH$_2$—O—T$_1$; or $R_7$ and $R_8$ are a radical of the formula (2a)

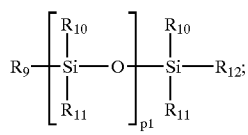

$R_9$ is the direct bond; a straight-chain or branched $C_1$–$C_4$alkylene radical or a radical of the formula —$C_{m_1}H_{2m_1}$—O—;

$R_{10}$, $R_{11}$, and $R_{12}$, independently of one another, are $C_1$–$C_{18}$alkyl; $C_1$–$C_{18}$alkoxy or a radical of the formula

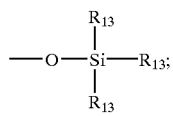

$R_{13}$ is $C_1$–$C_5$alkyl;
$m_1$ is 1 to 4;
$p_1$ is 0 to 5;
$A_1$ is a radical of the formula

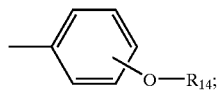 (2b)

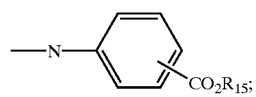 (2c)

or of the formula

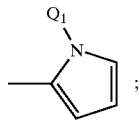 (2d)

$R_{14}$ is hydrogen; $C_1$–$C_{10}$alkyl, —(CH$_2$CHR$_{16}$—O)$_{n_1}$—R$_{15}$; or a radical of the formula —CH$_2$—CH(—OH)—CH$_2$—O—T$_1$;

$R_{15}$ is hydrogen; M; $C_1$–$C_5$alkyl; or a radical of the formula —(CH$_2$)$_{m_2}$—O—(CH$_2$)$_{m_3}$—T$_1$;

$R_{16}$ is hydrogen; or methyl;

$T_1$ is hydrogen; or $C_1$–$C_8$alkyl;

$Q_1$ is $C_1$–$C_{18}$alkyl;

M is a metal cation;

$m_2$ and $m_3$, independently of one another, are 1 to 4; and $n_1$ is 1 to 16.

Very particularly preferred triazine derivatives of the formula (2) correspond to the formulae

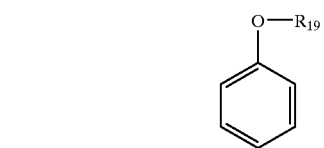 (2a)

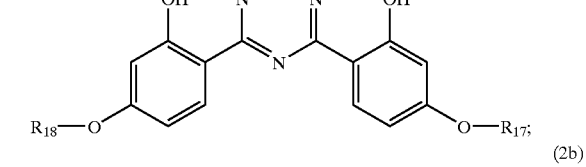 (2b)

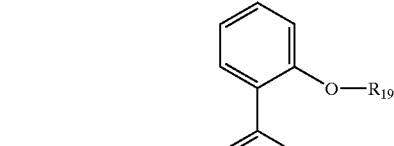 (2c)

or

 (2d)

in which $R_{17}$ and $R_{18}$, independently of one another, are $C_3$–$C_{18}$alkyl; or —CH$_2$—CH(—OH)—CH$_2$—O—T$_1$;

$R_{19}$ is $C_1$–$C_{10}$alkyl or a radical of the formula

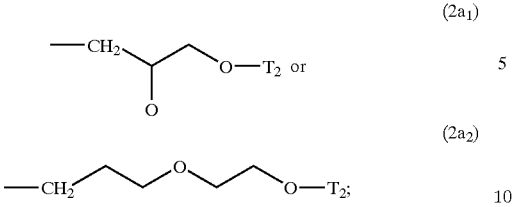

(2a$_1$)

(2a$_2$)

$R_{20}$ is hydrogen; M; $C_1$–$C_5$alkyl; —NH—$C_1$–$C_5$alkyl; preferably —NH-tert-alkyl; or a radical of the formula —(CH$_2$)$_m$—O—T$_2$;

$T_1$ and $T_2$, independently of one another, are hydrogen; or $C_1$–$C_5$alkyl; and m is 1 to 4.

Of very particular interest are compounds of the formula (2a) and (2b) in which $R_{17}$ and $R_{18}$, independently of one another, are $C_1$–$C_{18}$alkyl; or —CH$_2$—CH(—OH)—CH$_2$—O—T$_1$;

$R_{19}$ is $C_1$–$C_{10}$alkyl;

and compounds of the formula (2c) and (2d) in which $R_{17}$ and $R_{18}$, independently of one another, are $C_1$–$C_{18}$alkyl or —CH$_2$—CH(—OH)—CH$_2$—O—T$_1$; and $T_1$ is hydrogen; or $C_1$–$C_5$alkyl.

Of the utmost interest are triazine compounds of the formula (2a)–(2d) in which $R_{17}$ and $R_{18}$ have the same meanings.

Further interesting triazine compounds which can be used according to the invention correspond to the formula (3)

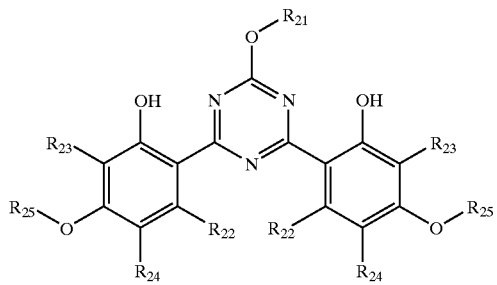

in which $R_{21}$ is $C_1$–$C_{30}$alkyl; $C_2$–$C_{30}$alkenyl; unsubstituted $C_5$–$C_{12}$cycloalkyl or $C_5$–$C_{12}$cycloalkyl mono- or polysubstituted by $C_1$–$C_5$alkyl; $C_1$–$C_5$alkoxy-$C_1$–$C_{12}$alkyl; amino-$C_1$–$C_{12}$alkyl; $C_1$–$C_5$monoalkylamino-$C_1$–$C_{12}$alkyl; $C_1$–$C_5$dialkylamino-$C_1$–$C_{12}$alkyl; a radical of the formula (3a)

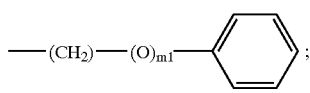

or (3b)

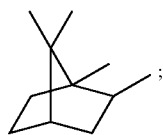

in which $R_{22}$, $R_{23}$ and $R_{24}$, independently of one another, are hydrogen, —OH; $C_1$–$C_{30}$alkyl, $C_2$–$C_{30}$alkenyl, $R_{25}$ is hydrogen; or $C_1$–$C_5$alkyl;

$m_1$ is 0 or 1; and $n_1$ is 1 to 5.

Preferred compounds correspond to the formula (4)

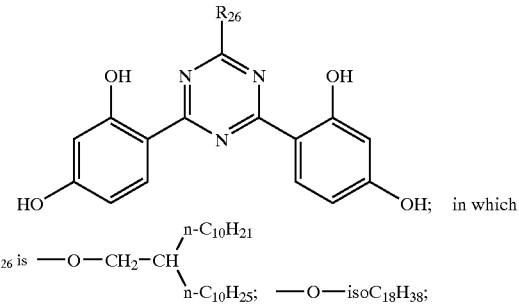

in which

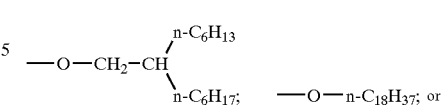

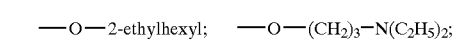

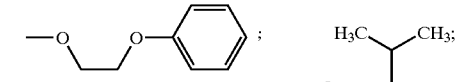

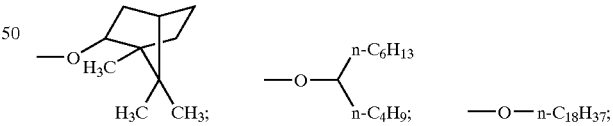

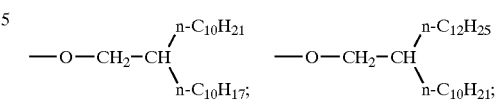

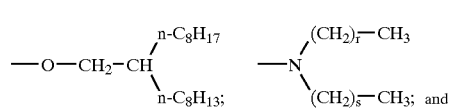

r and s, independently of one another, are 0 to 20.

Examples of triazine derivatives which can be used according to the invention correspond to the formulae
(5)
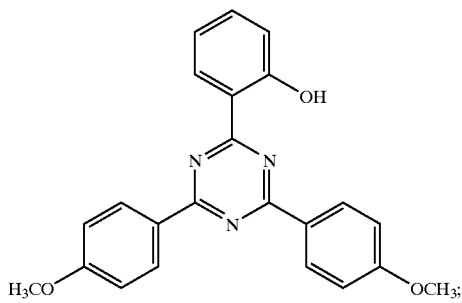
(6)
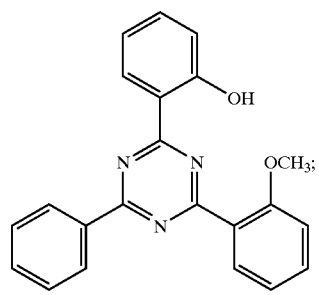
(7)
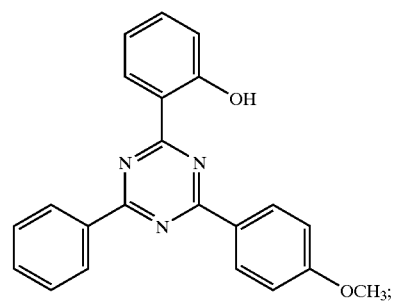
(8)
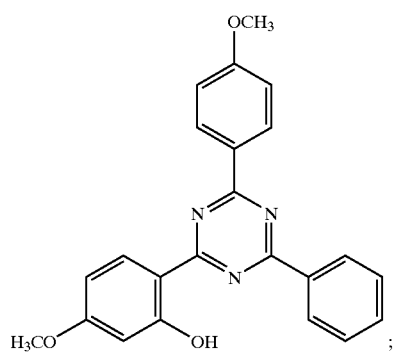
(9)
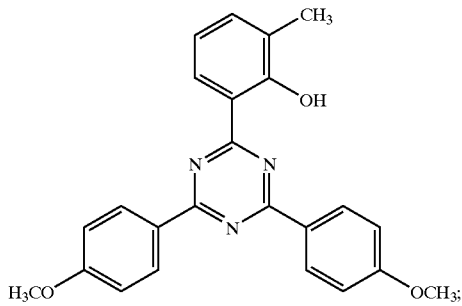
-continued
(10)
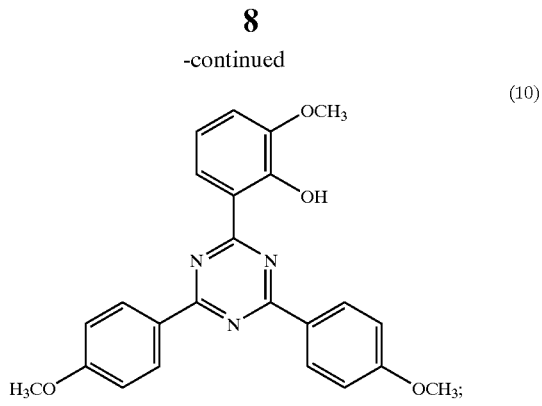
(11)
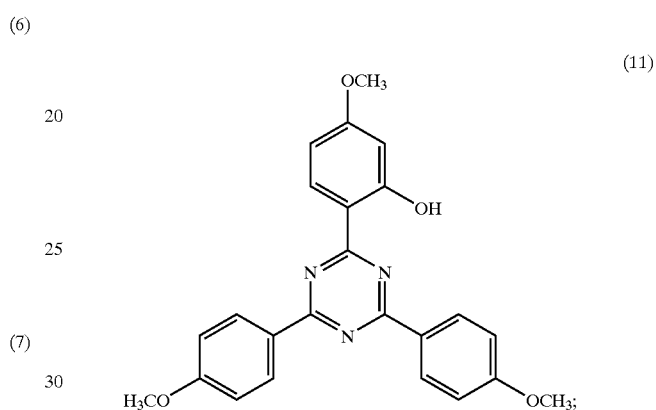
(12)
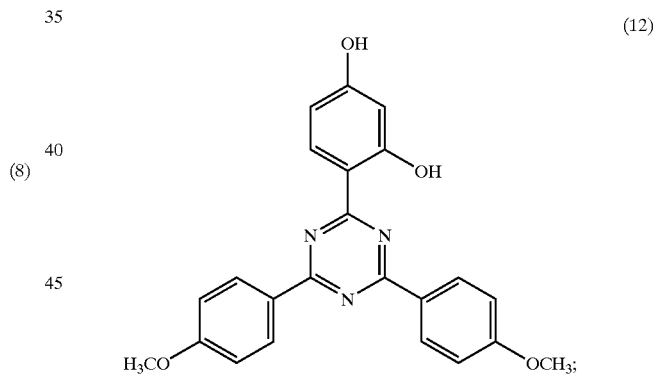
(13)
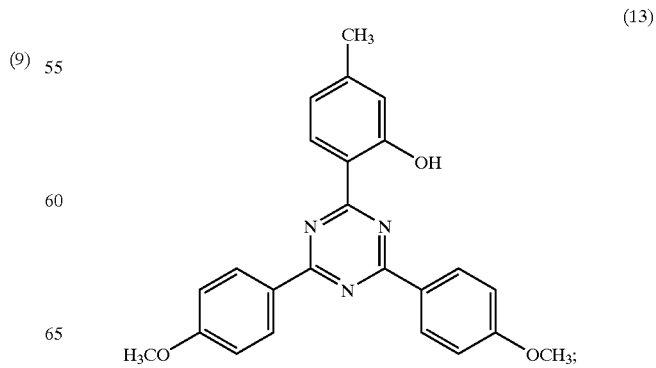

-continued
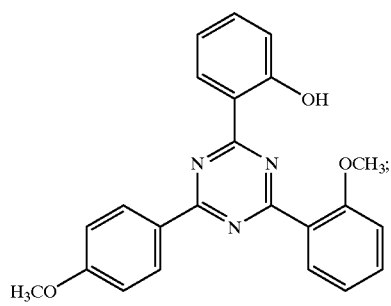
(14)
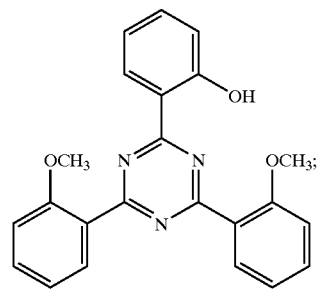
(15)
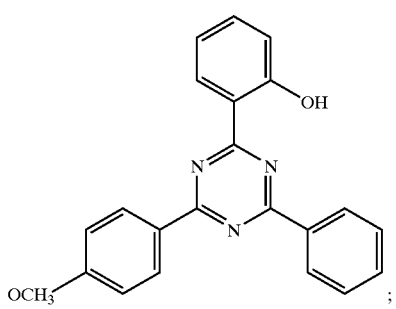
(16)
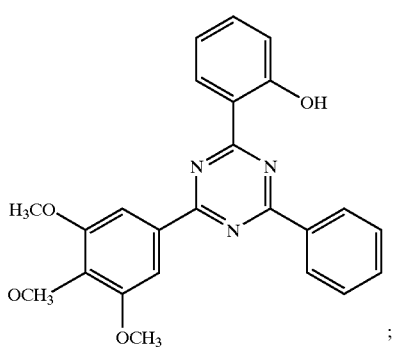
(17)
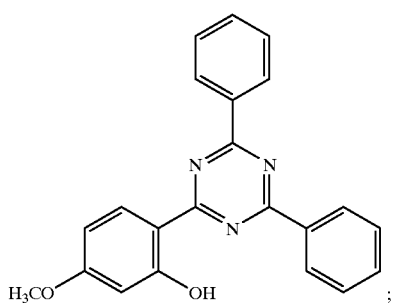
(18)
-continued
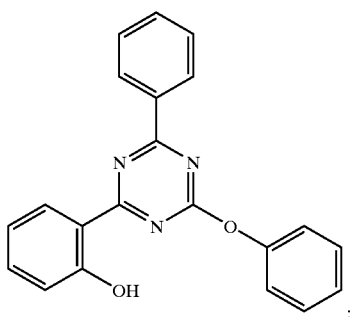
(19)
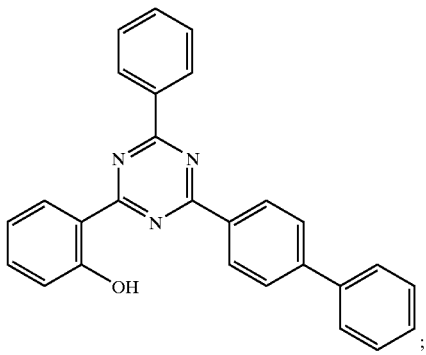
(20)
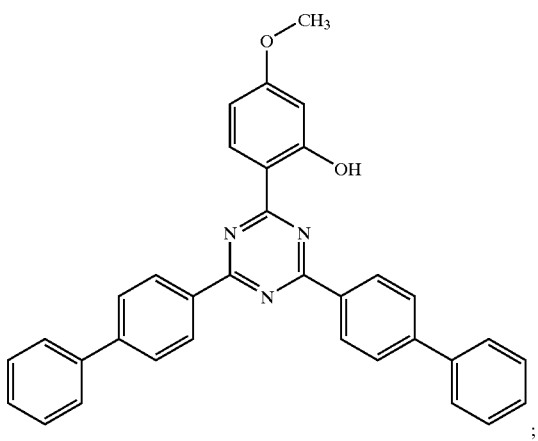
(20a)
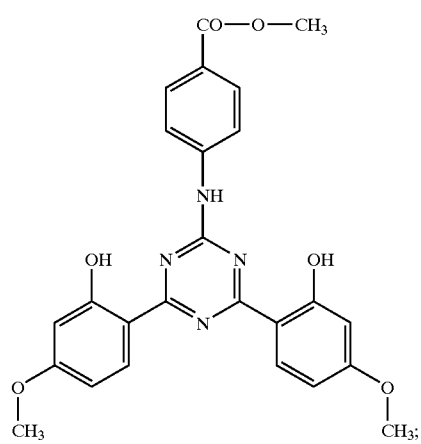
(21)

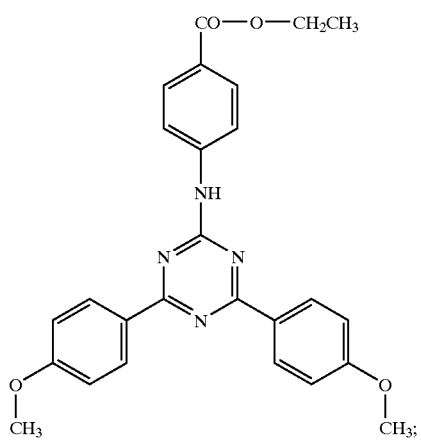
(22)

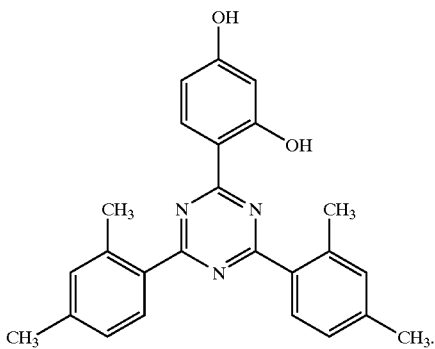
(24a)

According to the invention, particularly suitable triazine compounds are those described, for example, in EP-A-0, 818450, for example the compound of the formula

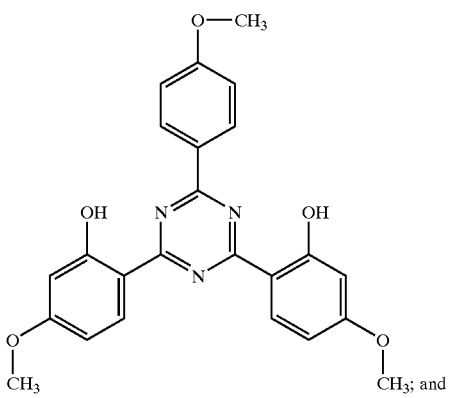
(23)

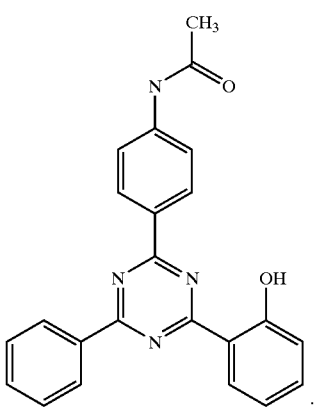
(24b)

Very particularly preferred triazine derivatives which can be used according to the invention correspond to the formula

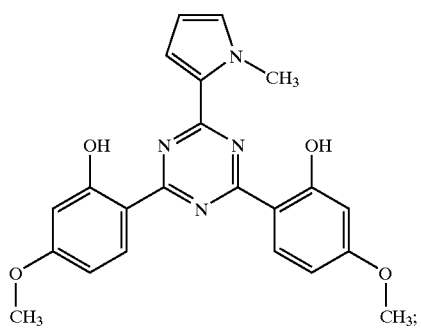
(24)

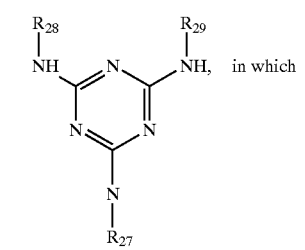
(25)

in which and also 2,4,6-tris(diisobutyl-4'-aminobenzalmalonate)-s-triazine and 2,4-bis(diisobutyl-4-aminobenzalmalonate)-6-(4'-aminobenzylidenecamphor)-s-triazine.

$R_{27}$, $R_{28}$ and $R_{29}$, independently of one another, are a radical of the formula Likewise preferred triazine compounds which can be used according to the invention are described in EP-A-654469, for example the compound of the formula

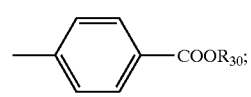
(25a)

-continued

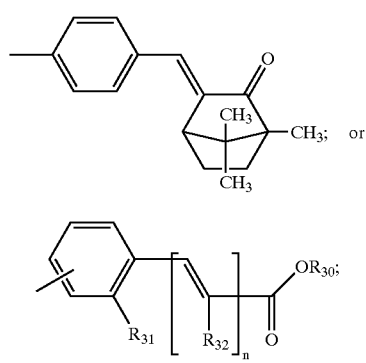
(25b)

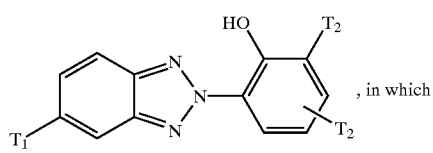
(25c)

$R_{30}$ is hydrogen; alkali metal; an ammonium group —$N(R_{33})_4$, $R_{33}$ is hydrogen; $C_1$–$C_5$alkyl; or a polyoxyethylene radical which has 1 to 10 ethylene oxide units and the terminal OH group can be etherified with a $C_1$–$C_5$alcohol;

$R_{31}$ is hydrogen; —OH; or $C_1$–$C_6$alkoxy;

$R_{32}$ is hydrogen or —$COOR_{30}$; and n is 0 or 1.

If $R_{30}$ is alkali metal, this is in particular potassium or very particularly sodium. $(R_{33})_4$ is in particular a mono-, di- or tri-$C_1$–$C_4$alkylammonium salt, a mono-, di- or tri-$C_2$–$C_4$alkanol-ammonium salt or a $C_1$–$C_3$alkyl ester thereof.

If $R_{33}$ is a $C_1$–$C_3$alkyl group, this is in particular a $C_1$–$C_2$alkyl group, in particular a methyl group, and if $R_{33}$ is a polyoxyethylene radical, then the latter contains in particular 2 to 6 ethylene oxide units.

Preferred benzotriazole compounds which can be used according to the invention correspond to the formula

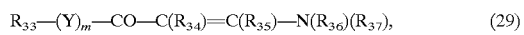
(26)

$T_1$ is $C_1$–$C_5$alkyl or, preferably, hydrogen; and $T_2$ is $C_1$–$C_5$alkyl, preferably t-butyl, or phenyl-substituted $C_1$–$C_4$alkyl, in particular α,α-dimethylbenzyl.

A further preferred class of benzotriazole compounds which can be used according to the invention corresponds to the formula

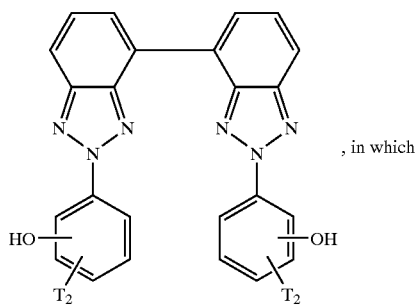
(27)

$T_2$ is as defined in formula (26).

Other very particularly preferred benzotriazole compounds which can be used according to the invention correspond to the formula

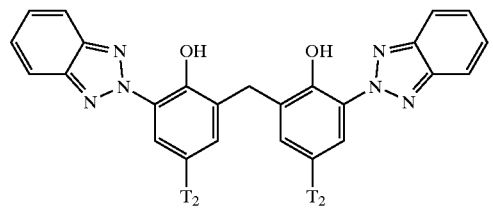
(28)

$T_2$ is as defined in formula (26) and is preferably methyl, t-butyl or isooctyl.

Preferred vinyl-containing amides which can be used according to the invention correspond to the formula $$R_{33}-(Y)_m-CO-C(R_{34})=C(R_{35})-N(R_{36})(R_{37}),$$ (29)

in which $R_{33}$ is $C_1$–$C_5$alkyl, preferably methyl or ethyl, or unsubstituted phenyl or phenyl substituted by one, two or three of the radicals OH, $C_1$–$C_5$alkyl, $C_1$–$C_5$alkoxy or CO—$OR_{33}$;

$R_{34}$, $R_{35}$, $R_{36}$ and $R_{37}$, independently of one another, are $C_1$–$C_5$alkyl, preferably methyl or ethyl; or hydrogen;

Y is —NH or —O—; and m is as defined above.

Preferred compounds of the formula (29) are 4-methyl-3-penten-2-one, ethyl 3-methyl-amino-2-butenoate, 3-methylamino-1-phenyl-2-buten-1-one and 3-methylamino-1-phenyl-2-buten-1-one.

Preferred cinnamides which can be used according to the invention correspond to the formula

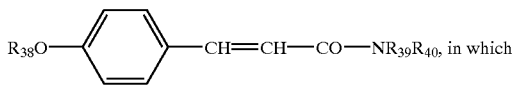
(30)

$R_{38}$ is hydrogen or $C_1$–$C_5$alkoxy, preferably methoxy or ethoxy;

$R_{39}$ is hydrogen or $C_1$–$C_5$alkyl, preferably methyl or ethyl; and $R_{40}$ is —$(CONH)_m$-phenyl, in which m is as defined above, and the phenyl group is unsubstituted or substituted by one, two or three of the radicals OH, $C_1$–$C_3$alkyl, $C_1$–$C_3$alkoxy or CO—$OR_{30}$.

$R_{40}$ is preferably phenyl, 4-methoxyphenyl or the phenylaminocarbonyl group.

Further preferred cinnamic acid derivatives are 2-ethylhexyl 4-methoxycinnamate or isoamylate or inter alia the cinnamic acid derivatives disclosed in U.S. Pat. No. 5,601,811 and WO 97/00851.

Preferred sulfonated benzimidazoles which can be used according to the invention correspond to the formula

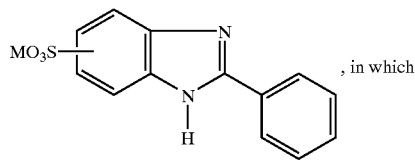
(31)

, in which

M is hydrogen or an: alkali metal, preferably sodium, an alkaline earth metal, for example magnesium or calcium, or zinc.

Preferred Fischer base aldehydes which can be used according to the invention correspond to the formula

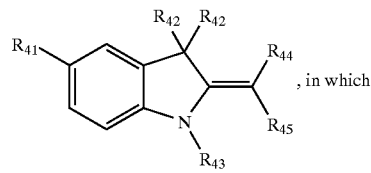
(32)

, in which $R_{41}$ is hydrogen; $C_1$–$C_5$alkyl; $C_1$–$C_{18}$alkoxy; or halogen;

$R_{42}$ is $C_1$–$C_8$alkyl; $C_5$–$C_7$cycloalkyl; or $C_6$–$C_{10}$aryl;

$R_{43}$ is $C_1$–$C_{18}$alkyl or a radical of the formula (32a)

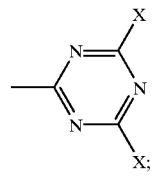

$R_{44}$ is hydrogen; or a radical of the formula

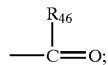

$R_{45}$ is

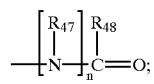

$C_1$–$C_{18}$alkoxy; or a radical of the formula

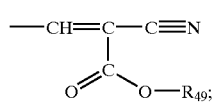
(32b)

$R_{46}$ and $R_{47}$, independently of one another, are hydrogen; or $C_1$–$C_5$alkyl;

$R_{48}$ is hydrogen; $C_1$–$C_5$alkyl; $C_5$–$C_7$cycloalkyl; phenyl; phenyl-$C_1$–$C_3$alkyl;

$R_{49}$ is $C_1$–$C_{18}$alkyl;

X is Hal; a radical of the formula (32c)

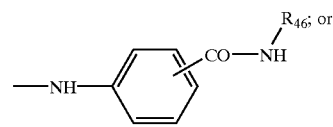

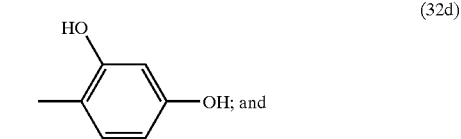
(32d)

n is 0 or 1.

Further compounds which can be used with preference correspond to the formula

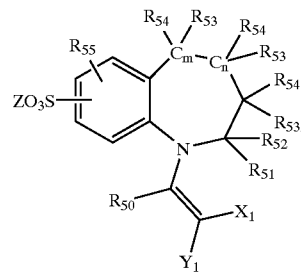
(33)

in which $R_{50}$, $R_{51}$, $R_{52}$, $R_{53}$, $R_{54}$, independently of one another, are hydrogen, $C_1$–$C_8$alkyl or $C_5$–$C_{10}$cycloalkyl;

$R_{55}$ is hydrogen; $C_1$–$C_8$alkyl; $C_5$–$C_{10}$cycloalkyl; hydroxyl; $C_1$–$C_8$alkoxy; $COOR_{56}$; or $R_{56}$, $R_{57}$ and $R_{58}$, independently of one another, are hydrogen or $C_1$–$C_6$alkyl;

X and Y, independently of one another, are hydrogen, —CN; $CO_2R_{59}$; $CONR_{59}R_{60}$; or $COR_{59}$; where the radicals X and Y may additionally be a $C_1$–$C_8$alkyl radical, a $C_5$–$C_{10}$alkyl radical, in particular phenyl, or a heteroaryl radical having 5 to 6 ring atoms, where, in addition, X and Y or $R_{50}$ together with one of the radicals X and Y can represent the radical to complete a 5- to 7-membered ring which may contain up to 3 heteroatoms, in particular oxygen and/or nitrogen, where the ring atoms may be substituted, in particular by exocyclically double-bonded oxygen (keto oxygen) and/or $C_1$–$C_8$alkyl and/or $C_5$–$C_{10}$cycloalkyl radicals, and/or may contain C=C double bonds;

Z is hydrogen; ammonium; alkali metal ion; in particular lithium, sodium, potassium, 1/2 equivalents of alkaline earth metal ion, preferably calcium, magnesium or the cation of an organic nitrogen base used to neutralize the free acid group, $R_{59}$ and $R_{60}$, independently of one another, are hydrogen, $C_1$–$C_8$alkyl or $C_5$–$C_{10}$cycloalkyl; and n and m, independently of one another, are 0 or 1.

Preferred diphenylmalonitriles which can be used according to the invention correspond to the formula

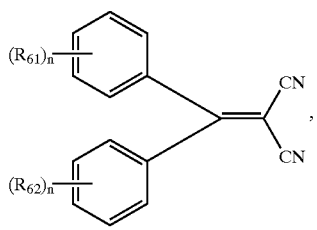

(34)

in which $R_{61}$ and $R_{62}$, independently of one another, are $C_1$–$C_{12}$alkyl; or $C_1$–$C_{12}$alkoxy; and n is 0–3.

Other organic UV filters which can be used according to the invention correspond to the formula

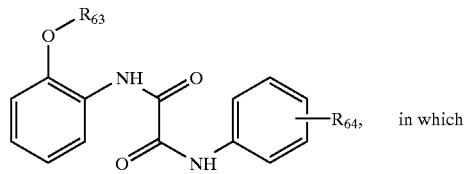

(35)

in which $R_{63}$ and $R_{64}$, independently of one another, are $C_1$–$C_5$alkyl, in particular ethyl.

Other preferred chemical compound classes of UV filters which can be used according to the invention are:

p-aminobenzoic acid derivatives (PABA), in particular 2-ethylhexyl 4-dimethylamino-benzoate;

salicylic acid derivatives, in particular 2-ethylhexyl salicylates; homosalates; and isopropyl salicylates;

benzophenone derivatives, in particular benzophenone-2, -3, and -4;

dibenzoylmethane derivatives, in particular 1-(4-tert-butylphenyl)-3-(4-methoxyphenyl)-propane-1,3-dione or butylmethoxydibenzoylmethane;

diphenylacrylates, in particular 2-ethylhexyl 2-cyano-3,3-diphenylacrylate, ethyl 2-cyano-3,3'-diphenylacrylate and 3-(benzofuranyl) 2-cyanoacrylate;

3-imidazol-4-ylacrylic acid and 3-imidazol-4-yl acrylate;

benzofuran derivatives, in particular the p-aminophenylbenzofuran derivatives published in EP-A-582,189, U.S. Pat. Nos. 5,338,539 and 5,518,713;

camphor derivatives, in particular 3-(4'-methyl)benzylidenebornan-2-one, 3-benzyidenebornan-2-one, N-[2(and 4)-2-oxyborn-3-ylidenemethyl)benzyl] acrylamide polymer, 3-(4'-trimethylammonium)benzylidenebornan-2-one methylsulfate, 3,3'-(1,4-phenylenedimethine)-bis(7,7-dimethyl-2-oxobicyclo[2.2.1]heptane-1-methanesulfonic acid) and salts thereof, 3-(4'-sulfo)benzylidenebornan-2-one and salts thereof; and menthyl o-aminobenzoate.

The UV filters listed above can be used according to the invention as individual compounds or also, preferably, as mixtures.

Preference is given to using the following mixtures of organic UV filters:

mixtures of methylenebisbenzotriazolyltetramethylbutylphenol and octyltriazone;

mixtures of octyltriazone and methylenebisbenzotriazolyltetramethylbutylphenol;

mixtures of 2-[(2,4-methoxy)phenyl]-4,6-bis[(2-hydroxy-4-methoxy)phenyl]-(1,3,5)triazine and methylenebisbenzotriazolyltetramethylbutylphenol;

mixtures of methylenebisbenzotriazolyltetramethylbutylphenol and dioctylbutamidotriazone;

mixtures of methylenebisbenzotriazolyltetramethylbutylphenol and octyl-2,2'-methylenebis[6-(2H-benzotriazol-2-yl)-4-methylphenol, mixtures of octyltriazone and trisresorcinyltriazine;

mixtures of 2,2'-methylenebis[6-(2H-benzotriazol-2-yl)-4-methylphenol, octyltriazone and the compound of the formula (36)

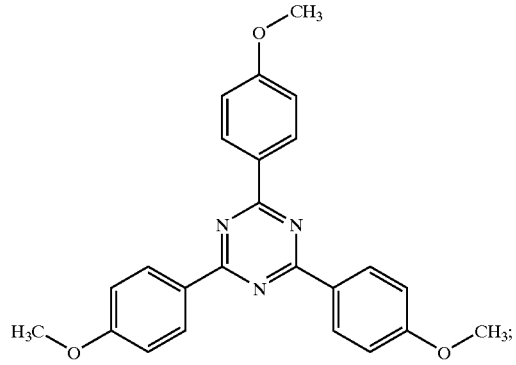

mixtures of 2,2'-methylenebis[6-(2H-benzotriazol-2-yl)-4-methylphenol, octyltriazone and the compound of the formula (37)

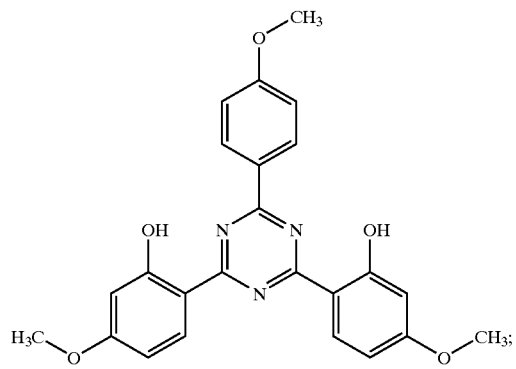

mixtures of methylenebisbenzotriazolyltetramethylbutylphenol, octyltriazone and the compound of the formula (38)

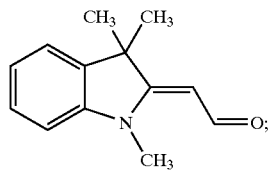

mixtures of methylenebisbenzotriazolyltetramethyl-butylphenol and the compound of the formula (39)

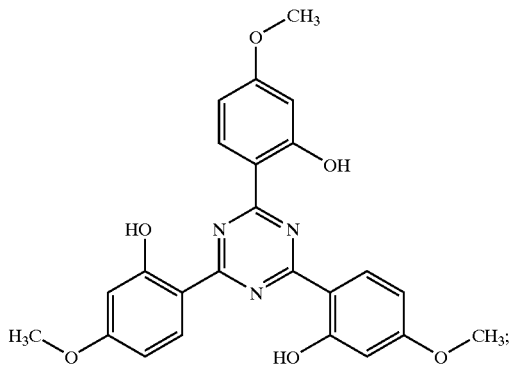

mixtures of methylenebisbenzotriazolyltetramethyl-butylphenol, dioctylbutamidotriazone and the compound of the formula (37).

In the radicals defined above, $C_1$–$C_{18}$alkyl are straight-chain or branched alkyl radicals, for example methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl or octadecyl.

$C_1$–$C_{18}$Alkoxy radicals are straight-chain or branched alkyl radicals, for example methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy or octadecyloxy.

$C_2$–$C_{18}$Alkenyl is, for example, allyl, methallyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl, n-dodec-2-enyl or n-octadec-4-enyl.

The mixtures of micronized organic UV filters which can be used according to the invention can be prepared in different ways.

Firstly, at least two of the abovementioned organic UV filters can be mixed as individual substances in the preparation process of the microparticles (micronization).

Another preparation option involves thoroughly mixing the already micronized individual substances of the UV filters together.

A third preparation option involves melting together at least two of the abovementioned UV filters. Cooling the melt produces a homogeneous composite, which is micronized in the usual manner.

The homogeneous composites of at least two organic UV filters are also provided by the invention.

The invention further provides composites obtainable by fusing one or more inorganic micropigments into one or more organic UV filters.

Examples of micropigments are, for example, $TiO_2$, ZnO, iron oxides or other inorganic oxides, mica or other suitable inorganic minerals, and also Ti, alkaline earth metal or zinc salts of organic acids.

In so doing, the undesired photocatalytic properties of some of these inorganic micropigments ($TiO_2$, ZnO) can be simultaneously suppressed, and their positive properties can also be fully utilized.

The abovementioned inorganic UV filters are advantageously fused into methylenebisbenzotriazolyltetramethylbutylphenol. The resulting composite is then micronized in the usual manner.

The invention further provides composites obtainable by melting at least two electrically neutral organic UV filters with cationically or anionically charged compounds.

For this, cationically or anionically charged compounds are melted with the corresponding organic, electrically neutral UV filters and then cooled. This process permits, in the subsequent micronization step, the preparation of organic UV filter pigments having a permanent finishing of a positive or negative charge. Such a finishing effectively prevents aggregation of the micronized particles in the sunscreen preparations which can occur in cases where the particle diameter is <1 µm. An otherwise customary "coating" of these particles having a repelling effect then sometimes becomes superfluous.

Cationically or anionically charged compounds which can be used are UV filters and also other compounds which have one or more cationic or anionic groups, for example N,N,N-trimethyl-4-(2-oxoborn-3-ylidenemethyl)aniline methylsulfate;

camphorbenzalkonium methosulfate;

fatty amines;

betaines, for example cocamidopropylbetaine;

quats, for example ricinoleamidopropyltrimonium methosulfate, Quarternium 18, or cetyltrimethylammonium bromide;

behenic acid and other organic acids, for example isostearic acid, citricmonoglyceride or sodium methyl cocoyl taurate;

phospholipids, for example phosphatidylcholine, phosphatidylserine or alkylamine oxide;

ceramides and pseudoceramides and phytosterols.

The last-named compounds impart an oleophobic finishing to the micronized UV filters.

The proportion of cationic or anionic compounds in the composite is between 0.001 and 5% by weight, preferably 0.01 to 3% by weight, based on the weight of the UV filter(s).

The invention further provides composites obtainable by melting at least one sparingly soluble or insoluble organic UV filter with antioxidants.

For this, the sparingly soluble or insoluble organic UV filter(s) is/are melted together with antioxidants, cooled and then micronized in the usual manner.

Suitable antioxidants which can be used according to the invention are all organic substances having scavenger properties which can be melted together with organic UV filters. This gives novel types of micropigments which simultaneously prevent tanning of the skin and offer antioxidative action on its surface. This property is desired for cosmetic sun protection since, under the influence of UV and light, harmful free radicals can be formed both in formulations and on the skin. These can, for example, lead to so-called Mallorca acne or to premature skin ageing. By finishing the micronized UV filters with antioxidants, not only is protection against UV damage and prevention of tanning achieved, but also protection against photochemical degradation of constituents in the sunscreen formulation.

The proportion of antioxidants in the composite is generally between 0.001 and 30% by weight, preferably 0.01 to 3% by weight, based on the weight of the UV filter(s).

A content of antioxidants is particularly advantageous in micropigments which, in addition to organic UV filters, comprise the abovementioned photocatalytically active inorganic micropigments, for example titanium dioxide, zinc oxide (including coated) or other suitable inorganic oxides, for example iron oxide.

Examples of antioxidants which may be listed are the following compounds:

tocopherols, for example α-tocopherol (CAS 59-02-9), tocopheryl acetate, vitamin E succinate, ellagic acid

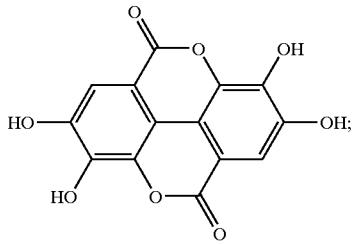

propyl gallate (CAS 121-79-9)

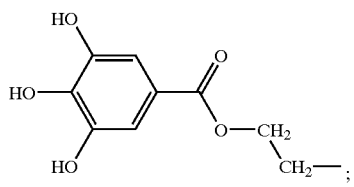

N-butylated hydroxytoluene (BHT; CAS 128-37-0);
butylated hydroxyanisole (BHA);
2,4,6-tris(3,5-di-t-butyl-4-hydroxybenzyl)mesitylene (CAS 1709-70-2)

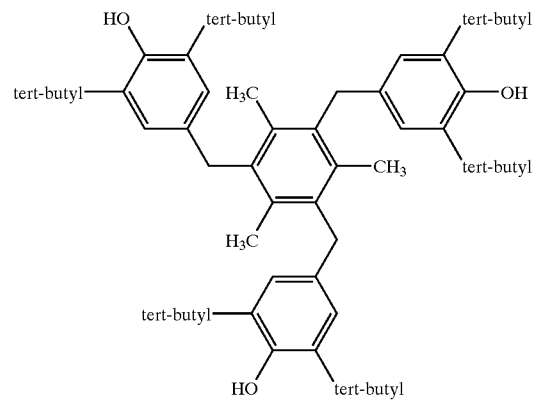

tetrakis[methylene-3(3',5'-di-t-butyl-4'-hydroxyphenyl)propionate]methane (CAS 6683-19-8);
compound of the formula

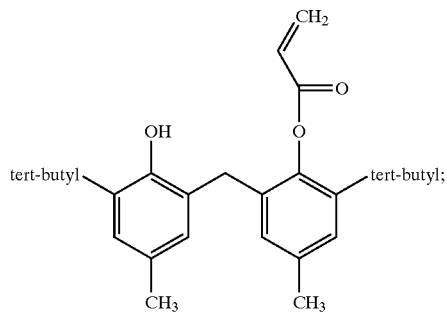

compound of the formula

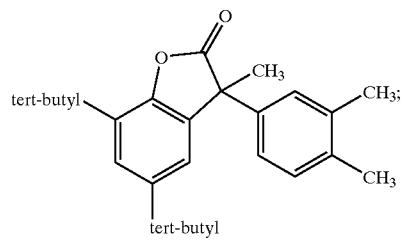

compound of the formula
vanillin;
ubiquinone;
ferulic acid and derivatives;
rutic acid and derivatives;
urocanic acid and derivatives; and
propolis.

Preference is given to using the following mixtures of antioxidants and organic UV filters:

mixtures of methylenebisbenzotriazolyltetramethylbutylphenol, octyltriazone, titanium dioxide and tocopherol, mixtures of 2,2'-methylenebis[6-(2H-benzotriazol-2-yl)4-methylphenol, octyltriazone, trisresorcinyltriazine and vitamin E mixtures of methylenebisbenzotriazolyltetramethylbutylphenol, octyltriazone, compound of the formula (103)

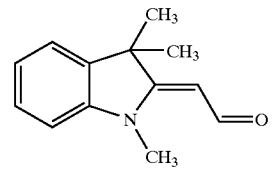

("Fischer aldehyde") and compound of the formula

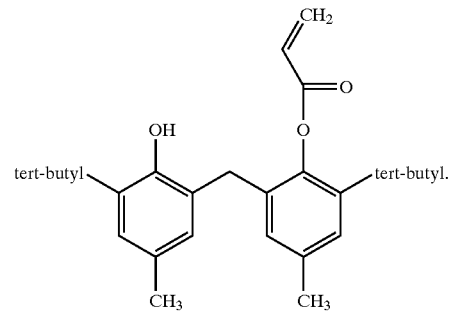

The invention further provides composites obtainable by fusing meltable cosmetic, vegetable and pharmaceutical active ingredients into organic UV filters.

In general, micronized UV filters can be used as carriers of highly active substances, in particular cosmetic and/or pharmaceutical active substances. The advantage of such composites lies in the fact that it is possible for them to release the active substance(s) from the solid (slow release). A slow release also guarantees the uniform effectiveness of highly active active ingredients, for example antiinflammatories, care active ingredients or trace elements, for example $Zn^{2+}$ or $Mg^{2+}$, over the entire useful life of the UV pigments.

Examples of active ingredients which can be used and which may be mentioned are:

- active ingredients for antimicrobial finishing and simultaneous antiinflammatory action, for example triclosan or diclosan;
- antiinflammatory active ingredients, for example farnesol, panthenol or avocado oil;
- active ingredients having a deodorant or antiperspirant action, for example Zn ricinoleates and alkyl citrates,
- undecylenic acid and derivatives thereof (e.g. diethanolamides)
- zinc undecylate;
- pyrithiones, for example sodium pyrithione;
- fused-in fragrances or fragrance mixtures, for example menthol, geraniol etc., which impart a permanent odour which is uniform in intensity to these micropigments and the formulations which comprise them.

To prepare the micronized organic UV filters or the micropigment mixtures, it is possible to use all known processes which are suitable for the preparation of microparticles, for example:

- wet grinding with a hard grinding medium, for example zirconium silicate and a protective surfactant or a protective polymer in water or a suitable organic solvent;
- spray drying from a suitable solvent, for example aqueous or organic suspensions containing solvent, or true solutions in water, ethanol, dichloroethane, toluene, N-methylpyrrolidone etc.;
- by expansion of supercritical liquids (e.g. $CO_2$) in accordance with the RESS process (Rapid Expansion of Supercritical Solutions) in which the UV filter(s) is/are dissolved or expansion of liquid carbon dioxide together with a solution of one or more UV filters in a suitable organic solvent;
- by reprecipitation from suitable solvents, including supercritical liquids (GASR process=Gas Anti-Solvent Recrystallizabon/PCA process=Precipitation with Compressed Antisolvents).

Grinding apparatuses which can be used for the preparation of the micronized organic UV absorbers according to the invention are, for example, a jet, ball, vibratory or hammer mill, preferably a high-speed stirred mill. Grinding preferably takes place using a grinding auxiliary, for example an alkylated vinylpyrrolidone polymer, a vinylpyrrolidone/vinyl acetate copolymer, an acyl glutamate, an alkyl polyglucoside, ceteareth-25 or, in particular, a phospholipid.

The resulting micropigments or mixtures of micropigments usually have an average particle size of from 0.02 to 2 nm, preferably 0.05 to 1.5 nm, and very particularly from 0.1 to 1.0 nm.

Because of their lipophilicity, they can, alone or together with other soluble organic UV absorbers, be readily incorporated into oil- and fat-containing cosmetic formulations, for example oils, O/W or W/O emulsions, wax pencils or gels, by known methods.

Surprisingly, formulations are obtained which have equal or improved protective action using less or even no soluble UV absorbers.

The invention further provides a cosmetic formulation comprising a mixture of micropigments, if desired one or more antioxidants and/or inorganic pigments and/or a cationic or anionic compound, and cosmetically compatible carriers or auxiliaries.

Cosmetic formulations according to the invention include various cosmetic compositions. In particular, the following compositions are, for example, suitable:

- skincare compositions, for example skin washes and cleansers in the form of bar or liquid soaps, syndets or washing pastes,
- bath preparations, for example liquid (foam baths, milks, shower preparations) or solid bath preparations, for example bath tablets or bath salts;
- skincare compositions, for example skin emulsions, multiple emulsions or skin oils;
- decorative bodycare compositions, for example face make-up in the form of day creams or powder creams, face powder (loose or pressed), blusher or cream make-up, eyecare compositions, for example eyeshadow preparations, mascara, eyeliner, eye creams or eye-fix creams; lipcare compositions, for example lipstick, lip gloss, lip liner pencil, nailcare compositions, such as nail varnish, nail varnish remover, nail hardeners or cuticle removers;
- personal hygiene care compositions, for example personal hygiene washing lotions or personal hygiene sprays;
- footcare compositions, for example foot baths, foot powders, foot creams or foot balsams, special deodorants and antiperspirants or products for removing calluses;
- light protection compositions, such as sun milks, lotions, creams and oils, sun blocks or tropicals, pretanning preparations or aftersun preparations;
- skin tanning compositions, for example self-tanning creams;
- depigmentation products, for example preparations for skin bleaching or compositions for skin lightening;
- insect-repelling compositions ("repellents"), for example insect oils, lotions, sprays or sticks;
- deodorants, such as deodorant sprays, pump sprays and deodorant gels, sticks or roller balls;
- antiperspirants, for example antiperspirant sticks, creams or roller balls;
- compositions for cleansing and caring for blemished skin, for example syndets (solid or liquid), peeling or exfoliation preparations or peeling masks;
- depilatories in chemical form, for example depilatory powders, liquid depilatores, cream or paste depilatories, depilatories in gel form or aerosol foams;
- shaving compositions, for example shaving soap, foaming shaving creams, nonfoaming shaving creams, foams, gels, preshave preparations for dry shaving, aftershaves or aftershave lotions;
- fragrances, for example fragrance water (eau de Cologne, eau de toilette, eau de parfum, parfum de toilette, parfum), perfume oils or perfume creams;
- compositions for dental, denture and mouth care, for example toothpastes, gel toothpastes, tooth powders, mouthwash concentrates, antiplaque mouthrinses, denture cleaners or denture adhesives;
- cosmetic compositions for treating hair, for example hair cleansers in the form of shampoos, hair conditioners, haircare compositions, for example pretreatment compositions, hair tonic, styling creams, styling gels, pomades, hair rinses, treatment packs, intensive hair treatments, compositions for shaping hair, for example waving agents for the preparation of permanent waves (hotwave, mildwave, coldwave), hair-smoothing preparations, liquid hair-setting compositions, hair mousses, hair sprays, bleaching agents, for example hydrogen peroxide solutions, lightening shampoos, bleaching creams, bleaching powders, bleaching pastes or oils, temporary, semipermanent or permanent hair colorants, preparations containing self-oxidizing dyes, or natural hair colorants, such as henna or camomile.

These listed end formulations can be in the form of various application forms, for example in the form of liquid preparations as a W/O, O/W, O/W/O, W/O/W, PIT and all other types of microemulsions, in the form of a gel, in the form of an oil, a cream, milk or lotion, in the form of a powder, a lacquer, a tablet or make-up, in the form of a stick, in the form of a spray (spray with propellant or pump spray) or an aerosol, in the form of a foam, or in the form of a paste.

The cosmetic formulations according to the invention can advantageously comprise further substances which absorb UV radiation in the UVB region. The total amount of filter substances here is 0.1 to 30% by weight, preferably 0.5 to 10% by weight, in particular 1 to 6% by weight, based on the total weight of the composition.

In particular, suitable additional UVB filters are oil-soluble, nonmicronized compounds, for example organic UV absorbers from the class of p-aminobenzoic acid derivatives, salicylic acid derivatives, benzophenone derivatives, dibenzoylmethane derivatives, diphenylacrylate derivatives, benzofuran derivatives, polymeric UV absorbers, comprising one or more organosilicon radicals, cinnamic acid derivatives, camphor derivatives, trianilino-s-triazine derivatives, phenylbenzimidazolesulfonic acid and salts thereof, menthyl anthranilate, benzotriazole derivatives, and/or an inorganic micropigment chosen from zinc oxide, mica or $TiO_2$ coated with aluminium oxide or silicon dioxide.

Examples of compounds of p-aminobenzoic acid derivatives:

4-aminobenzoic acid (PABA); ethyldihydroxypropyl-PABA of the formula

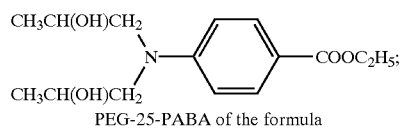

PEG-25-PABA of the formula

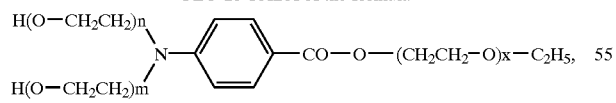

in which m,n and x have the same meaning and are each at most 25;

octyldimethyl PABA of the formula

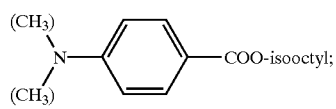

or glycyl aminobenzoate of the formula

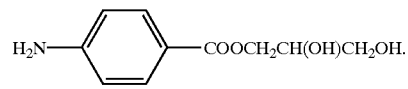

Examples of compounds of salicylic acid derivatives:
homomenthyl salicylate of the formula

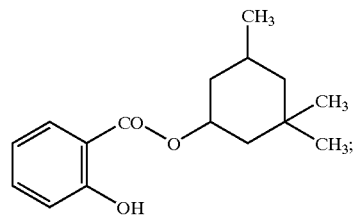

triethanolamine salicylate of the formula

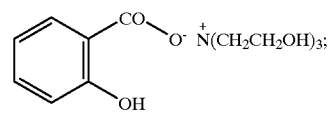

amyl p-dimethylamino-benzoate of the formula (10)

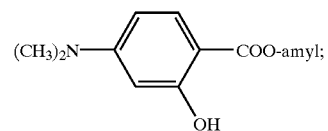

octyl salicylate of the formula

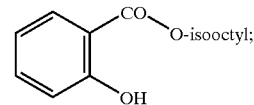

or 4-isopropylbenzyl salicylate of the formula

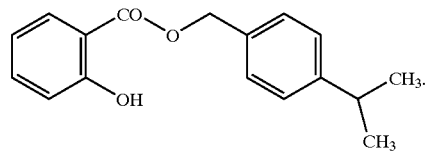

Examples of compounds of benzophenone derivatives:
benzophenone-3-(2-hydroxy4-methoxybenzophenone), benzophenone4-(2-hydroxy-4-methoxybenzophenone-5-sulfonic acid) or benzophenone-8-(2,2'-dihydroxy-4-methoxybenzophenone).

Examples of compounds of dibenzoylmethane derivatives:
butylmethoxydibenzoylmethane[1-(4-tert-butyl)-3-(4-methoxyphenyl)propane-1,3-dione].

Examples of compounds of diphenylacrylate derivatives:
octocrylene 2-ethylhexyl-2-cyano-3,3'-diphenylacrylate or etocrylene ethyl-2-cyano-3,3'-diphenylacrylate.

Examples of compounds of benzofuran derivatives:
3-benzofuranyl 2-cyanoacrylate, 2-(2-benzofuranyl)-5-tert-butylbenzoxazole or 2-(p-aminophenyl)benzofuran and, in particular, the compound of the formula

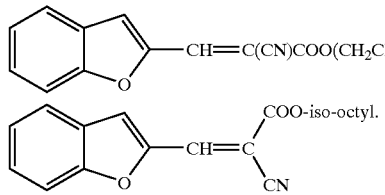

or

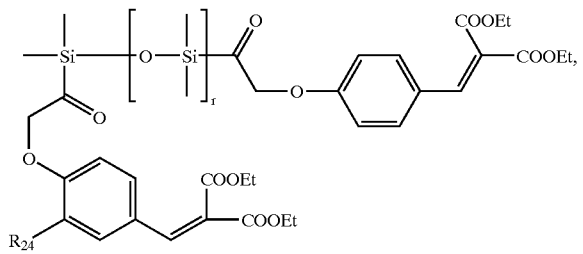

Examples of compounds of polymeric UV absorbers which comprise one or more organosilicon radicals:

benzylidenemalonate derivatives, in particular the compound of the formula

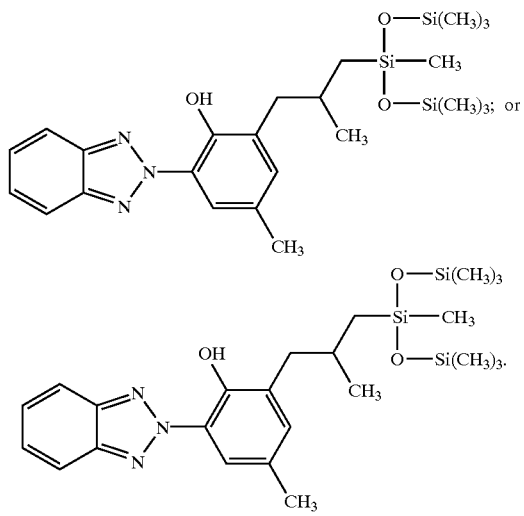

in which
$R_{24}$ is hydrogen or methoxy and
r is approximately 7; the compound of the formula Examples of compounds of cinnamic esters:
octyl methoxycinnamate (2-ethylhexyl 4-methoxycinnamate), diethanolamine methoxycinnamate (diethanolamine salt of 4-methoxycinnamic acid), isoamyl p-methoxycinnamate (2-isoamyl 4-ethoxycinnamate), 2,5-diisopropyl methylcinnamate or a cinnamic acid amido derivative.

Examples of compounds of camphor derivatives:
4-methylbenzylidenecamphor [3-(4'-methyl)benzylidenebornan-2-one],
3-benzylidenecamphor (3-benzylidenebornan-2-one),
polyacrylamidomethylbenzylidenecamphor {N-[2(and 4)-2-oxyborn-3-ylidene-methyl)benzyl]acrylamide polymer}, trimoniumbenzylidenecamphor sulfate [3-(4'-trimethylammonium)benzylidenebornan-2-one methylsulfate], terephthalylidene-dicamphorsulfonic acid {3,3'-(1,4-phenylenedimethine)bis(7,7-dimethyl-2-oxobicyclo[2.2.1]heptane-1-methanesulfonic acid} or salts thereof, or benzylidene-camphorsulfonic acid [3-(4'-sulpho)benzylidenebornan-2-one] or salts thereof.

Examples of compounds of trianilino-s-triazine derivatives:
octyltriazine[2,4,6-trianilino(p-carbo-2'-ethyl-1'-oxy)-1,3,5-triazine, and the trianilino-s-triazine derivatives described in U.S. Pat. Nos. 5,332,568, 5,252,323, WO 93/17002 and WO 97/03642 and EP-A-0,517,104.

Examples of compounds of benzotriazoles:
2-(2-hydroxy-5-methylphenyl)benzotriazole.

The examples below serve to illustrate the invention without limiting it thereto. The cosmetic active substances are primarily given with their INCI name (INCI= International Nomenclature of Cosmetic Ingredients).

EXAMPLE 1

50 parts of Methylene Bis-benzotriazolyl Tetramethylbutylphenol and 50 parts of Octyl Triazone are ground together using a grinding medium of zirconium silicate sand, a protective surfactant (Alkyl Polyglucoside) and water in a bead mill to give a mixed micropigment having a $d_{50}$ of 190 nm. After the grinding medium has been separated off, the suspension of the mixed micropigment can be used to prepare sunscreen formulations.

EXAMPLE 2

32 parts of Octyl Triazone, 1 part of cetyltrimethylammonium bromide and 66 parts of Methylene Bis-benzotriazolyl Tetramethylbutylphenol are homogeneously melted together. The mixture is rapidly cooled to room temperature, and the solidifiedmeltiscomminuted mechanically (beater mill). This resulting powder is slurried in water, Decyl Glycoside is added, and the mixture is micronized together with a grinding auxiliary ('heavy sand') to a particle size diameter $d_{50}$ of 200 nm. After the grinding auxiliary has been removed, an aqueous suspension of the micronized UV absorber composite is obtained. This suspension is rendered slightly acidic with citric acid and can be used for the preparation of cosmetic and pharmaceutical formulations.

EXAMPLE 3

25 parts of 2-[(2,4-methoxy)phenyl]-4,6-bis[(2-hydroxy-4-methoxy)phenyl]-(1,3,5)-triazine, 74 parts of Methylene Bis-benzotriazolyl Tetramethylbutylphenol and 1 part of homogeneously fused together. The mixture is rapidly cooled to room temperature, and the solidified melt is comminuted mechanically (beater mill). This resulting powder is slurried in water, firstly Decyl Glycoside is added, then, after continued grinding, Ceteareth-25, and the mixture is micronized together with a grinding auxiliary ('heavy sand') to a particle size diameter $d_{50}$ of 190 nm. After the grinding auxiliary has been separated off, an aqueous suspension of the micronized UV absorber composite is obtained, which can be used for the preparation of cosmetic and pharmaceutical formulations.

EXAMPLE 4

25 parts of Dioctyl Butamido Triazone are dissolved in 75 parts of molten Methylene Bis-benzotriazolyl Tetramethylbutylphenol. The mixture is cooled rapidly, comminuted mechanically to give a fine powder and then ground with a grinding medium of zirconium silicate sand, a protective surfactant (phospholipid) and water to give a micropigment having a $d_{50}$ of 300 nm. The micropigment suspension separated off from the grinding medium is used for the preparation of sunscreen formulations.

EXAMPLE 5

24 parts of Octyl Triazone, 5 parts of Titanium Dioxide and one part of Tocopherol are mixed into 70 parts of molten Methylene Bis-benzotriazolyl Tetramethylbutylphenol. The mixture is cooled rapidly, comminuted mechanically to give a fine powder and then ground with a grinding medium of zirconium silicate sand, a protective surfactant (Alkyl Polyglucoside) and water to give a micropigment. The micropigment suspension separated off from the grinding medium is used for the preparation of sunscreen formulations.

In Examples 6 to 11 below, suspensions of microcomposites having the following compositions are prepared analogously to Examples 1 and 2:

EXAMPLE 6

60 parts of 2,2'-methylenebis[6-(2H-benzotriazol-2-yl)-4-methylphenol, 20 parts of Octyl Triazone, 19 parts of Tris Resorcinyl Triazine and 1 part of vitamin E, adjusted to pH 6.5 with citric acid.

EXAMPLE 7

60 parts of 2,2'-methylenebis[6-(2H-benzotriazol-2-yl)-4-methylphenol, 20 parts of Octyl Triazone and 20 parts of the compound of the formula (101)

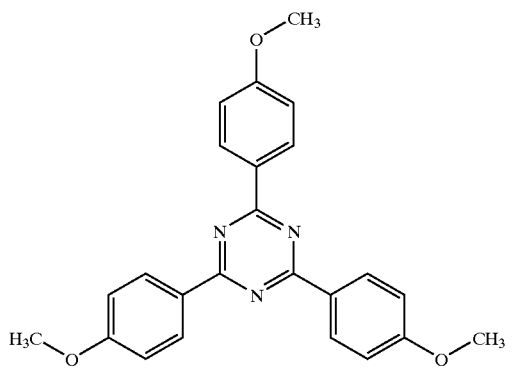

EXAMPLE 8

59 parts of 2,2'-methylenebis[6-(2H-benzotriazol-2-yl)-4-methylphenol, 20 parts of Octyl Triazone, 20 parts of the compound of the formula (102)

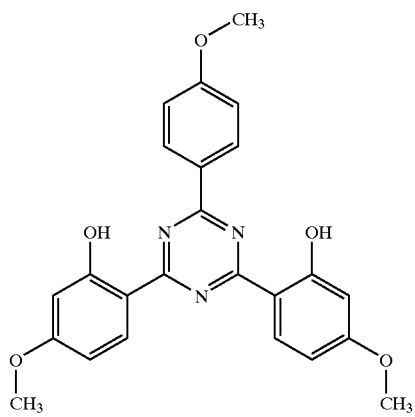

and adjusted to pH 6.5 with citric acid.

EXAMPLE 9

75 parts of Methylene Bis-benzotriazolyl Tetramethylbutylphenol, 10 parts of Octyl Triazone (grinding at pH<5, adjusted with citric acid), 14 parts of the compound of the formula (103)

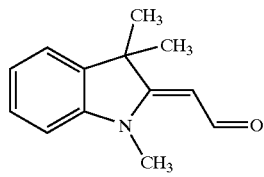

("Fischer aldehyde") and 1 part of the compound of the formula

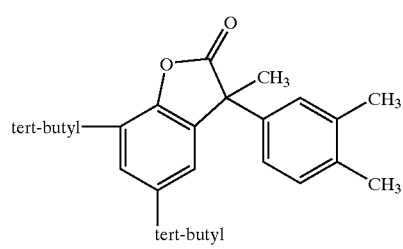

EXAMPLE 10

80 parts of Methylene Bis-benzotriazolyl Tetramethylbutylphenol, and 20 parts of the compound of the formula (104)

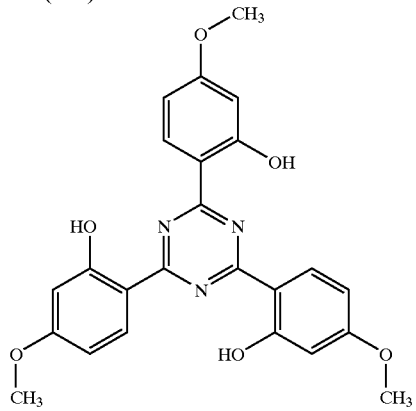

EXAMPLE 11

50 parts of Methylene Bis-benzotriazolyl Tetramethylbutylphenol, 10 parts of Dioctyl Butamido Triazone (grinding at pH<5, adjusted to pH 6.5 with citric acid) and 20 parts of the compound of the formula (102).

EXAMPLE 12
O/W Lotion for Preventing Tanning

| | | % |
|---|---|---|
| A | Polyglyceryl-3 Methylglucose Distearate | 2.0 |
| | Decyl Oleate | 5.7 |
| | Isopropyl Palmitate | 6.0 |
| | Caprylic/Capric Triglyceride | 7.5 |
| B | Glycerin | 3.0 |
| | Phenonip | 0.5 |
| | Water | 69.3 |
| C | Carbomer | 0.2 |
| | Isopropyl Palmitate | 0.8 |
| D | Micropigment from Example 2 | 5.0 |
| E | NaOH (10%) | as required |

EXAMPLE 13
O/W Emulsion

| | % |
|---|---|
| Potassium Cetyl Phosphate | 2.00 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Glyceryl Stearate | 3.00 |
| Cetyl Alcohol | 1.00 |
| Phenoxyethanol & Parabens | 1.00 |
| Octyl Methoxycinnamate | 5.00 |
| Dimethicone | 0.10 |
| Deionized Water | 64.15 |
| Carbomer (Carbopol 981) | 0.10 |
| Glycerin | 3.00 |
| NaOH (10%) | 1.00 |
| Micropigment from Example 1 | 4.00 |

EXAMPLE 14

O/W Emulsion

| | % |
|---|---|
| Cetearyl Alcohol & Dicetyl Phosphate & Ceteth-10 Phosphate | 6.00 |
| Caprylic/Capric Triglyceride | 5.00 |
| Cetearyl Isononanoate | 5.00 |
| C12–15 Alkyl Benzoate | 5.00 |
| Phenoxyethanol & Parabens | 1.00 |
| Octyl Methoxycinnamate | 5.00 |
| Dimethicone | 0.20 |
| Deionized Water | 64.70 |
| Carbomer (Carbopol 981) | 0.10 |
| Glycerin | 3.00 |
| NaOH (10%) | 0.65 |
| Micropigment from Example 3 | 4.00 |

EXAMPLE 15

O/W Emulsion

| | % |
|---|---|
| Isopropyl myristate & Trilaureth-4 Phosphate | 5.00 |
| Tricontanyl PVP | 1.00 |
| Caprylic/Capric Triglyceride | 5.00 |
| Cetearyl Isononanoate | 2.00 |
| C12–15 Alkyl Benzoate | 5.00 |
| Glyceryl Stearate | 2.00 |
| Cetyl Alcohol | 1.00 |
| Phenoxyethanol & Parabens | 1.00 |
| Octyl Methoxycinnamate | 5.00 |
| Dimethicone | 0.10 |
| Deionized Water | 66.30 |
| Carbomer (Carbopol 981) | 0.10 |
| Glycerin | 3.00 |
| NaOH (10%) | 0.50 |
| Micropigment from Example 4 | 4.00 |

EXAMPLE 16

O/W Emulsion

| | % |
|---|---|
| Sodium Stearyl Lactate Tricontanyl PVP | 1.50 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Glyceryl Stearate | 3.50 |
| Cetyl Alcohol | 2.00 |
| Phenoxyethanol & Parabens | 1.00 |
| Octyl Methoxycinnamate | 5.00 |
| Dimethicone | 0.20 |
| Deionized Water | 63.60 |
| Carbomer (Carbopol 981) | 0.10 |
| Glycerin | 3.00 |
| NaOH (10%) | 0.10 |
| Micropigment from Example 6 | 4.00 |

EXAMPLE 17

O/W Emulsion

|  | % |
|---|---|
| Cetearyl Alcohol & Sodium Cetearyl Sulfate | 5.00 |
| Caprylic/Capric Triglyceride | 5.00 |
| Cetearyl Isononanoate | 5.00 |
| C12–15 Alkyl Benzoate | 5.00 |
| Phenoxyethanol & Parabens | 1.00 |
| Octyl Methoxycinnamate | 5.00 |
| Dimethicone | 0.10 |
| Deionized Water | 65.90 |
| Glycerin | 3.00 |
| NaOH (10%) | 0.30 |
| Micropigment from Example 9 | 4.00 |

EXAMPLE 18

O/W Emulsion

|  | % |
|---|---|
| Lauryl Glucoside & Polyglyceryl-2 Dihydroxystearate & Glycerin | 3.00 |
| Tricontanyl PVP | 1.00 |
| Caprylic/Capric Triglyceride | 4.00 |
| Cetearyl Isononanoate | 4.00 |
| C12–15 Alkyl Benzoate | 5.00 |
| Glyceryl Stearate | 2.00 |
| Cetyl Alcohol | 3.00 |
| Phenoxyethanol & Parabens | 1.00 |
| Octyl Methoxycinnamate | 5.00 |
| Dimethicone | 0.20 |
| Deionized Water | 64.49 |
| Carbomer (Carbopol 981) | 0.10 |
| Glycerin | 3.00 |
| NaOH (10%) | 0.21 |
| Micropigment from Example 8 | 4.00 |

EXAMPLE 19

O/W Emulsion

|  | % |
|---|---|
| Cetaryl Glucoside & Cetearyl Alcohol | 4.50 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Phenoxyethanol & Parabens | 1.00 |
| Octyl Triazone | 3.00 |
| 4-Methylbenzylidene camphor | 3.00 |
| Dimethicone | 0.20 |
| Deionized Water | 64.65 |
| Steareth-10 Allyl Ether/Acrylates Copolymer | 5.00 |
| Glycerin | 3.00 |
| NaOH (10%) | 1.00 |
| Micropigment from Example 2 | 4.00 |

EXAMPLE 20

O/W Emulsion

|  | % |
|---|---|
| Cetearyl Glucoside | 5.00 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Phenoxyethanol & Parabens | 1.00 |
| Octocrylene | 3.00 |
| Octyl Methoxycinnamate | 4.00 |
| Dimethicone | 0.20 |
| Deionized Water | 63.15 |
| Carbomer (Carbopol 981) | 0.50 |
| Glycerin | 3.00 |
| NaOH (10%) | 0.15 |
| Micropigment from Example 2 | 4.00 |

EXAMPLE 21

O/W Emulsion

|  | % |
|---|---|
| Polyglyceryl-10 Petastearate & Behenyl Alcohol & Sodium Stearoyl Laurate | 2.50 |
| Caprylic/Capric Triglyceride | 5.00 |
| Cetearyl Isononanoate | 5.00 |
| C12–15 Alkyl Benzoate | 5.00 |
| Glyceryl Stearate | 3.00 |
| Cetearyl Alcohol | 2.00 |
| Phenoxyethanol & Parabens | 1.00 |
| Octyl Methoxycinnamate | 5.00 |
| Dimethicone | 0.20 |
| Deionized Water | 64.75 |
| Carbomer (Carbopol 981) | 0.15 |
| Glycerin | 3.00 |
| NaOH (10%) | 0.40 |
| Micropigment from Example 9 | 4.00 |

EXAMPLE 22

O/W Emulsion

|  | % |
|---|---|
| Palmitic Acid & Stearic Acid | 1.80 |
| Glyceryl Stearate SE | 3.00 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Glyceryl Stearate | 0.50 |
| Phenoxyethanol & Parabens | 1.00 |
| Octyl dimethyl PABA | 5.00 |
| Dimethicone | 0.10 |
| Deionized Water | 64.15 |
| Carbomer (Carbopol 981) | 0.10 |
| Glycerin | 3.00 |
| NaOH (10%) | 0.50 |
| Micropigment from Example 1 | 4.00 |

EXAMPLE 23

O/W Emulsion

|  | % |
|---|---|
| Glyceryl Stearate & PEG 100 Stearate | 3.00 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Cetearyl Alcohol | 3.00 |
| Phenoxyethanol & Parabens | 1.00 |
| Octyl Methoxycinnamate | 5.00 |
| Dimethicone | 0.10 |
| Deionized Water | 64.60 |
| Carbomer (Carbopol 981) | 0.10 |
| Glycerin | 3.00 |
| NaOH (10%) | 0.20 |
| Micropigment from Example 3 | 4.00 |

EXAMPLE 24

O/W Emulsion

|  | % |
|---|---|
| Steareth-2 | 2.50 |
| Steareth-21 | 1.00 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Cetyl Alcohol | 1.00 |
| Phenoxyethanol & Parabens | 1.00 |
| Methyl Anthranilate | 3.00 |
| Octyl Methoxycinnamate | 4.00 |
| Dimethicone | 0.10 |
| Deionized Water | 63.95 |
| Carbomer (Carbopol 981) | 0.20 |
| Glycerin | 3.00 |
| NaOH (10%) | 0.25 |
| Micropigment from Example 4 | 4.00 |

EXAMPLE 25

O/W Emulsion

|  | % |
|---|---|
| Glyceryl Stearate & Ceteareth-20 & Ceteareth-12 & Cetaryl Alcohol & Cetyl Palmitate | 5.00 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Phenoxyethanol & Parabens | 1.00 |
| 4-Methylbenzylidene camphor | 5.00 |
| Dimethicone | 0.10 |
| Deionized Water | 65.60 |
| Carbomer (Carbopol 981) | 0.10 |
| Glycerin | 3.00 |
| NaOH (10%) | 0.20 |
| Micropigment from Example 3 | 4.00 |

EXAMPLE 26

O/W Emulsion

|  | % |
|---|---|
| Octyldecyl Phosphate | 3.00 |
| Tricontanyl PVP | 1.00 |
| Caprylic/Capric Triglyceride | 5.00 |
| Cetearyl Isononanoate | 5.00 |
| C12–15 Alkyl Benzoate | 5.00 |
| Phenoxyethanol & Parabens | 1.00 |
| Octyl methoxycinnamate | 5.00 |
| Dimethicone | 0.10 |
| Deionized Water | 64.50 |
| Sodium Cocoyl Glutamate | 0.60 |
| Steareth-10 Allyl Ether/Acrylates Copolymer | 0.50 |
| Glycerin | 3.00 |
| NaOH (10%) | 2.30 |
| Micropigment from Example 4 | 4.00 |

EXAMPLE 27

O/W Emulsion

|  | % |
|---|---|
| Polyglyceryl-3 Methyl Glucose Distearate | 2.00 |
| Tricontanyl PVP | 1.00 |
| Tocopherol & Ascorbyl Palmitate & Ascorbic Acid & Citric Acid & PEG-8 | 0.05 |
| Decyl Oleate | 4.50 |
| Isopropyl Palmitate | 6.00 |
| Caprylic/Capric Triglyceride | 5.00 |
| Glyceryl Stearate | 1.00 |
| Cetearyl Alcohol | 1.00 |
| 2-[(2,4-Methoxy)phenyl]-4,6-bis[(2-hydroxy-4-methoxy)phenyl]-(1,3,5)triazine | 2.00 |
| Octyl Metnoxycinnamate | 3.00 |
| Deionized Water | 63.12 |
| Phenoxyethanol & Parabens | 0.80 |
| Propylene Glycol | 3.00 |
| Carbomer (Carbopol 981) | 0.20 |
| NaOH (10%) | 0.33 |
| Scleroglucan | 1.00 |
| Micropigment from Example 2 | 3.00 |
| Titanium Dioxide | 3.00 |

EXAMPLE 28

O/W Emulsion

|  | % |
|---|---|
| Methyl Glucose Sequistearate | 2.50 |
| Tricontanyl PVP | 1.00 |
| Tocopherol & Ascorbyl Palmitate & Ascorbic Acid & Citric Acid & PEG-8 | 0.05 |
| Decyl Oleate | 4.00 |
| Isopropyl Palmitate | 6.00 |
| Caprylic/Capric Triglyceride | 5.00 |
| Glyceryl Stearate | 1.00 |
| Cetearyl Alcohol | 1.00 |
| 2-[(2,4-Methoxy)phenyl]-4,6-bis[(2-hydroxy-4-methoxy)phenyl]-(1,3,5)triazine | 2.00 |
| Octyl Methoxycinnamate | 5.00 |
| Deionized Water | 63.12 |
| Phenoxyethanol & Parabens | 0.80 |
| Carbomer (Carbopol 981) | 0.20 |
| Glycerin | 3.00 |
| NaOH (10%) | 0.33 |
| Scleroglucan | 1.00 |
| Micropigment from Example 1 | 4.00 |

EXAMPLE 29
O/W Emulsion

| | % |
|---|---|
| Glycerin | 10.00 |
| PEG-45 & Dodecyl Glycerol Copolymer | 1.50 |
| Quaternium-18 Bentonite | 2.00 |
| Microcrystalline Wax | 2.00 |
| Beeswax | 2.00 |
| Glyceryl Stearate SE | 53.00 |
| Pentaerythrithil Stearate & Caprate & Caprylate Adipate | 4.00 |
| Castor Oil | 4.00 |
| Methylene Bis-benzotriazolyl Tetramethylbutylphenol | 5.00 |
| Micropigment from Example 2 | 5.00 |
| Titanium Dioxide | 5.00 |
| Zinc Oxide | 5.00 |
| Octyl Methoxycinnamate | 4.00 |
| Eucerinum anhydricum | ad 100 |

EXAMPLE 30
O/W Emulsion

| | % |
|---|---|
| PEG-30 Dipolyhydroxystearate | 2.00 |
| Isostearyl Alcohol | 20.00 |
| Isostearic Acid | 10.00 |
| Octyl Triazone | 3.00 |
| Deionized Water | 58.75 |
| Glycerin | 5.00 |
| Methylparaben | 0.17 |
| Propylparaben | 0.03 |
| $MgSO_4 \times 7H_2O$ | 0.75 |
| Micropigment from Example 2 | 4.00 |

EXAMPLE 31
O/W Emulsion

| | | % |
|---|---|---|
| A | Polyglyceryl-3 Methylglucose Distearate | 2.0 |
| | Decyl Oleate | 5.7 |
| | Isopropyl Palmitate | 5.0 |
| | Caprylic/Capric Triglyceride | 6.5 |
| | Octyl Methoxycinnamate | 5.0 |
| B | Glycerol | 3.0 |
| | Phenonip | 0.5 |
| | Deion. Water | 62.9 |
| C | Carbomer 141 | 0.2 |
| | Isopropyl Palmitate | 0.8 |
| D | 50% suspension from Example 8 | 8.0 |
| E | NaOH (10%) | as required |

EXAMPLE 32
O/W Emulsion

| | | % |
|---|---|---|
| A | Polyglyceryl-3 Methylglucose Distearate | 2.0 |
| | Decyl Oleate | 5.7 |
| | Isopropyl Palmitate | 5.0 |
| | Caprylic/Capric Triglyceride | 6.5 |
| B | Glycerol | 3.0 |
| | Phenonip | 0.5 |
| | Deioniz. Water | 62.9 |

-continued

| | | % |
|---|---|---|
| C | Carbomer 141 | 0.2 |
| | Isopropyl Palmitate | 0.8 |
| D | Suspension from Example 2 | 6.0 |
| E | NaOH (10%) | as required |

EXAMPLE 33
O/W Emulsion

| | | % |
|---|---|---|
| A | Polyglyceryl-3 Methylglucose Distearate | 2.0 |
| | Decyl Oleate | 5.7 |
| | Isopropyl Palmitate | 5.0 |
| | Caprylic/Capric Triglyceride | 6.5 |
| | Octyl Triazone | 2.0 |
| B | Glycerol | 3.0 |
| | Phenonip | 0.5 |
| | Water | 62.3 |
| C | Carbomer 141 | 0.2 |
| | Isopropyl Palmitate | 0.8 |
| D | 2,2'-Methylenebis(6-(2H-benzotriazol-2-yl)-4-(1,1,3,3-tetramethylbutyl)phenol Micropigment Suspension (50%) | 8.0 |
| | Octyl Triazone Micropigment Suspension (50%) | 4.0 |
| E | NaOH (10%) | as required |

EXAMPLE 34
O/W Emulsion

| | | % |
|---|---|---|
| A | Polyglyceryl-3 Methylglucose Distearate | 2.0 |
| | Decyl Oleate | 5.7 |
| | Isopropyl Palmitate | 5.0 |
| | Octyl Triazone | 2.0 |
| | Caprylic/Capric Triglyceride | 6.5 |
| B | Glycerol | 3.0 |
| | Phenonip | 0.5 |
| | Water | 68.3 |
| C | Carbomer 141 | 0.2 |
| | Isopropyl Palmitate | 0.8 |
| D | Micropigment from Example 2 | 6.0 |
| E | NaOH (10%) | as required |

EXAMPLE 35
O/W Emulsion

| | % |
|---|---|
| PEG-30 Dipolyhydroxystearate (Arlacel P 135 ®) | 3.00 |
| PEG-22/Dodecyl Glycol Copolymer (Elfacos ST 37 ®) | 1.00 |
| Microcrystalline Wax | 1.00 |
| Hydrogenated Castor Oil | 0.50 |
| Magnesium Stearate | 1.00 |
| Octyl Stearate | 15.00 |
| Coco Glycerides | 2.00 |
| Mineral Oil | 3.00 |
| Phenoxyethanol & Parabens | 1.00 |
| Octyl Methoxycinnamate | 5.00 |
| Dimethicone | 0.10 |
| Water | 54.40 |
| Magnesium Sulfate ($MgSO_4 \times 7\ H_2O$) | 1.00 |

|   | % |
|---|---|
| Propylene Glycol | 4.00 |
| 50% Suspension from Example 3 | 8.00 |

EXAMPLE 36
O/W Emulsion

|   | % |
|---|---|
| Methoxy PEG-22/Dodecyl Glycol Copolymer (Elfacos E 200 ®) | 3.00 |
| PEG-22/Dodecyl Glycol Copolymer (Elfacos ST 37 ®) | 3.00 |
| Hydroxyoctacosanyl Hydroxystearate (Elfacos C 26 ®) | 3.00 |
| Octyl Stearate | 15.00 |
| Coco Glycerides | 2.00 |
| Mineral Oil | 3.00 |
| Phenoxyethanol & Parabens | 1.00 |
| 4-Methylbenzylidene Camphor | 3.00 |
| Dioctyl Butamido Triazone | 3.00 |
| Dimethicone | 0.20 |
| Water | 53.00 |
| Phenylbenzimidazolesulfonic acid | 3.00 |
| Magnesium Sulfate (MgSO$_4$ × 7H$_2$O) | 0.80 |
| Propylene Glycol | 4.00 |
| Micropigment from Example 5 | 3.00 |

EXAMPLE 37
O/W Emulsion

|   | % |
|---|---|
| Polyglyceryl-2 Dipolyhydroxystearate (Dehymuls PGPH ®) | 2.00 |
| PEG-30 Dipolyhydroxystearate (Arlacel P 135 ®) | 2.00 |
| Hydroxyoctacosanyl Hydroxystearate (Elfacos C 26 ®) | 2.00 |
| Zinc Stearate | 1.00 |
| Octyl Stearate | 15.00 |
| Coco Glycerides | 2.00 |
| Mineral Oil | 3.00 |
| Phenoxyethanol & Parabens | 1.00 |
| 2,4-BIS{[4-(2-Ethylhexyloxy)-2-hydroxy]phenyl}-6-(4 methoxyphenyl)1,3,5)triazine | 2.00 |
| Octyl Salicylate | 3.00 |
| Dimethicone | 0.20 |
| Water | 56.70 |
| Magnesium Sulfate (MgSO$_4$ × 7 H$_2$O) | 1.00 |
| Propylene Glycol | 4.00 |
| Micropigment from Example 6 | 5.00 |

EXAMPLE 38
O/W Emulsion

|   | % |
|---|---|
| Polyglyceryl-2 Dipolyhydroxystearate (Dehymuls PGPH ®) | 3.00 |
| Glyceryl Oleate (Monomuls 90-O 18 ®) | 1.00 |
| Caprylic/Capric Triglyceride | 6.00 |
| Octyldodecanol | 6.00 |
| Cetearyl Isononaoate | 5.00 |
| Tocopheryl Acetate | 1.00 |
| Cera alba | 1.20 |
| Glycerin (86%) | 5.00 |
| Phenonip | 0.50 |
| Octyl Methoxycinnamate | 4.00 |
| Octyl Triazone | 3.00 |

|   | % |
|---|---|
| Micropigment from Example 3 | 5.00 |
| Water | ad 100 |

EXAMPLE 39
O/W Emulsion

|   | % |
|---|---|
| Polyglyceryl-2 Dipolyhydroxystearate (Dehymuls PGPH ®) | 3.00 |
| Glyceryl Oleate (Monomuls 90-O 18 ®) | 1.00 |
| Caprylic/Capric Triglyceride | 6.00 |
| Octyldodecanol | 6.00 |
| Cetearyl Isononaoate | 5.00 |
| Octyl Methoxycinnamate | 3.00 |
| Tocopheryl Acetate | 1.00 |
| Cera alba | 1.20 |
| Glycerin (86%) | 5.00 |
| Phenonip | 0.50 |
| Micropigment from Example 10 | 5.00 |
| Water | ad 100 |

EXAMPLE 40
O/W Emulsion

|   | % |
|---|---|
| Tego Care CG 90 (Goldschmidt AG) | 6.00 |
| Cetearyl Alcohol | 1.50 |
| Glycerylstearate | 0.50 |
| Octyldecanol | 7.00 |
| Capric/Caprylic Triglyceride | 5.00 |
| Cetearyl isononaoate | 6.00 |
| Octyl Methoxycinnamate | 3.00 |
| Deionized Water | 51.14 |
| Carbomer | 0.20 |
| NaOH (45%) | 1.13 |
| Glycerin | 5.00 |
| Methylparaben | 0.17 |
| Propylparaben | 0.03 |
| Terephthalylidenedibomanesulfonic acid | 1.50 |
| Micropigment from Example 5 (50% Suspension) | 12.00 |

EXAMPLE 41
O/W Emulsion

|   | % |
|---|---|
| Ceteareth-12 | 8.0 |
| Cetearyl Alcohol | 4.0 |
| Cetearyl isononaoate | 20.0 |
| Butyl Methoxydibenzoylmethane | 2.0 |
| Deionized Water | ad 100.0 |
| Carbomer | 0.2 |
| Preservative | as required |
| Magnesium Sulfate (MgSO$_4$ × 7 H$_2$O) | 3.0 |
| Micropigment from Example 9 (50% Suspension) | 8.0 |

EXAMPLE 42

O/W/O Emulsion

| | % |
|---|---|
| Polyglyceryl-2 polyhydroxystearate | 5.0 |
| Mineral oil | 12.5 |
| Stearic acid | 2.0 |
| Cetearyl isononaoate | 12.5 |
| Methylbenzylidene Camphor | 2.0 |
| Homosalate | 2.0 |
| Deionized Water | ad 100.0 |
| Carbomer | 0.2 |
| Preservative | as required |
| NaOH | as required |
| Micropigment from Example 2 (50% Suspension) | 8.0 |

EXAMPLE 43

O/W Emulsion

| | % |
|---|---|
| Glycerin Stearate/Polyethylene glycol (MW100) stearate | 3.0 |
| Cetyl/Stearyl Alcohol 20EO (Eumulgin B 2) | 1.0 |
| Cetyl/Stearyl Alcohol (Lanette O) | 2.0 |
| Caprylic/Capric triglyceride (Myritol 318) | 4.0 |
| Dicaprylyl ether | 6.0 |
| Mineral oil and Quaternium-18 Hectorite | 3.0 |
| Glycerin stearate, Cetyl/stearyl Alcohol, Cetyl palmitate, coco glycerides (Cutina CBS) | 2.0 |
| 4-Methylbenzylidene Camphor | 1.0 |
| Octyl Triazone | 2.0 |
| Deionized Water | ad 100.0 |
| Glycerin, 85% | 3.0 |
| Preservative | as required |
| Magnesium aluminium silicate (Vegum Ultra) | 0.3 |
| NaOH | as required |
| Micropigment from Example 2 (50% Suspension) | 10.0 |

EXAMPLE 44

Into the suncare product "Sensitive Skin" (children) from Lancaster (Monaco), characterized by the following ingredients: $TiO_2$, ZnO and Aqua, Didecene, Glycerine, Cyclomethicone, Shea Butter, Sweet Almond Oil, Polyglycerin-4, Urea, Aluminium Starch, Octenyl succinate, Alumina, Parfum, $MgSO_4$, Silica, NaCl, Tocopheryl acetate, Caffeine, PVP/Eicosene Copolymer, Shellac, Simethicone, Phenoxyethanol, NaLactate, Methylsilanol, Menthyl Lactate, Allantoin, Bisablolol, Glycine, Panthenol, Propylene Glycol, Stoneroot Extract, Lecithin, Algae Extract, Methyldibromo Glutaronitrile, PVP, Citric Acid, Copper Gluconate, Ascorbic Acid, Ascorbyl Palmitate, PEG-8, Tocopherol, Acerola, Aloe Barbadensis Gel, Melanin, Alcohol denat. Dimethicone, Guar Hydroxypropyltrimonium Chloride, Dextrin, Glycoproteins Iron oxides, were subsequently mixed 4% of micronized 2,2'-methylenebis[6-(2H-benzotriazol-2-yl)-4-(1,1,3,3-tetramethylbutyl)phenol (d50=200 nm). The original SPF of 15 increased as a result to 25 and, following storage for a few days, increased again to an SPF of 31.

EXAMPLE 45

Into the sun milk "Active Sun Care Sensitive Skin" from Marbert Cosmetics, Düsseldorf, characterized by the following ingredients: $TiO_2$, Benzophenone-3, Isoamyl p-Methoxycinnamate, and Aqua, $C_{12-15}$ Alkyl benzoate, Caprylic/Capric Triglyceride, Cyclomethicone, Glycerine, Glyceryl Stearate, Cetearyl Alcohol, Tocopheryl acetate, Stearic Acid, Palmitic Acid, Parfum, NaCocoyl Lactylate, Xanthan Gum, Bisabolol, DMDM Hydantoin, PVM/MA Decadiene Crosspolymer, Polyhydroxystearic acid, Alumina, NaOH, Glucose, Iodopropynyl Butylcarbamate, Carrageenan, Silica and Glucuronic acid, were subsequently mixed 4% of micronized 2,2'-methylenebis[6-(2H-benzotriazol-2-yl)-4-(1,1,3,3-tetramethylbutyl)phenol (d50=200 nm). The original SPF of 6 increased as a result to 13 and, after storage for a few days, increased again to an SPF of 16.

EXAMPLE 46

Into the sunscreen emulsion "Delial Sonnenmilch 10" from Sara Lee, Düsseldorf, characterized by the following ingredients: Octyl Methoxycinnamate, NaPhenylbenzimidazole Sulfonate, Butyl Methoxy Dibenzoylmethane and Aqua, Paraffinum liquidum, Alcohol denat., Isopropyl Palmitate, Glycerine, Cetearyl Alcohol, Glyceryl Stearate SE, Tocopheryl acetate, Phytantriol, Ascorbyl Palmitate, PEG-40 Castor Oil, NaCetearyl Sulfate, Dimethicone, Na-Carbomer, $Na_2$-EDTA and Parfum, were subsequently mixed 4% of micronized 2,2'-methylenebis[6-(2H-benzotriazol-2-yl)-4-(1,1,3,3-tetramethylbutyl)phenol (d50=200 nm). The original SPF of 10 increased as a result to 18 and, after storage for a few days, increased again to an SPF of 28.

EXAMPLE 47

Into the sun protection formulation "Ambre Solaire" SPF 12 from Laboratoires Garnier, Paris/Karlsruhe, characterized by the following ingredients: $TiO_2$, Octocrylene, Butyl Methoxy Dibenzoylmethane, Terephthalylidene dicamphor sulfonic acid and Aqua, Cyclopentasiloxane, Glycerine, Propylene glycol, Isohexadecane, Stearic acid, Octyl palmitate, Stearyl heptanoate, PVP/Eicosene Copolymer, K-Cetyl Phosphate, Buxus chinensis, Tocopheryl acetate, Hydroxypropyl Methylcellulose, Phenoxyethanol, Stearyl caprylate, PEG-100 Stearate, Ethylparaben, Triethanolamine, Dimethiconol, Dimethicone, Propylparaben, Acrylates/$C_{10-30}$-Alkyl acrylate crosspolymer, $Na_2$-EDTA, Butyrospermum parkii, Cetyl Alcohol, Methylparaben, Butylparaben, BHT, Aluminium hydroxide, Glyceryl Stearate were subsequently mixed 4% of micronized 2,2'-methylenebis[6-(2H-benzotriazol-2-yl)-4-(1,1,3,3-tetramethylbutyl)phenol (d50=200 nm). The original SPF of 12 increased as a result to 18 and, after storage for a few days, increased again to an SPF of 28.

EXAMPLE 48

Into the sunscreen formulation "Ambre Solaire" SPF 6 from Laboratoires Garnier, Paris/Karlsruhe, characterized by the following ingredients: $TiO_2$, Octocrylene, Butyl Methoxy Dibenzoylmethane, Terephthalylidene dicamphor sulfonic acid and Aqua, Cyclomethicone, Glycerine, Propylene glycol, Isohexadecane, Stearic acid, Octyl palmitate, Stearyl heptanoate, PVP/Eicosene Copolymer, K-Cetyl Phosphate, Buxus chinensis, Tocopheryl acetate, Hydroxypropyl Methylcellulose, Phenoxyethanol, Stearyl caprylate, PEG-100 Stearate, Ethylparaben, Triethanolamine, Dimethiconol, Dimethicone, Propylparaben, Acrylates/$C_{10-30}$-Alkyl acrylate crosspolymer, $Na_2$-EDTA, Butyrospermum parkii, Cetyl alcohol, Methylparaben, Butylparaben, BHT, Aluminium hydroxide, Glyceryl stearate and Parfum, were subsequently mixed 4% of micronized 2,2'-methylenebis[6-(2H-benzotriazol-2-yl)-4-(1,1,3,3-tetramethylbutyl)phenol (d50=200 nm). The original SPF of 6 increased as a result to 16 and, after storage for a few days, increased again to an SPF of 21.

EXAMPLE 49
Prevention of the Increase in Skin Tanning by a Micronized UV Absorber Methylene Bis-benzotriazolyl Tetramethylbutylphenol
Method
20 volunteers of direct Asian origin (father and mother) who have not been directly exposed to the sun for the past 3 months, to whom an explanation of the study has been given, from whom a declaration of consent has been obtained and who have satisfied the inclusion conditions, are treated twice daily on the test sites on the upper thigh for three weeks with a cream containing 2,2'-methylenebis(6-(2H-benzotriazol-2-yl)-4-(1,1,3,3-tetramethylbutyl)-phenol or with a placebo cream.

The volunteers are irradiated on the test sites on the upper thigh 3× weekly with 0.2 to 05 MED UVAB.

The first application of the preparations takes place after the first irradiation. Evaluation and irradiation are carried out after each application of the test products. Comparable untreated irradiated, or untreated nonirradiated areas serve as reference.

The colour values of the test fields are documented in each case using a Minolta CM-508i camera as L*a*b* values in accordance with DIN 5033, ISO 7724/1, JIS Z8722.

The colour and lightness changes are determined for each subject and ascertained as the difference between the respective skin colour of the untreated, nonirradiated reference area and the test areas. These values are averaged over all subjects and given as L*, a* and b'values.

Test Preparations
(A): Composition comprising 6% of 2,2'-Methylenebis(6 (2H-benzotriazol-2-yl)-4-(1,1,3,3-tetramethylbutyl) phenol), Water, Octyl stearate, Coco glycerides, Propylene glycol, Methoxy-PEG-22/Dodecyl glycol copolymer, PEG-22/Dodecyl glycol copolymer, Hydroxyoctacosanyl hydroxystearate, Mineral oil, Phenoxyethanol & Parabens, Magnesium sulfate heptahydrate, Dimethicone, Allantoin.
(B): Composition comprising 3% of 2,2'-Methylenebis(6-(2H-benzotriazol-2-yl)-4-(1,1,3,3-tetramethylbutyl) phenol), Water, Octyl stearate, Coco glycerides, Propylene glycol, Methoxy-PEG-22/Dodecyl glycol copolymer, PEG-22/Dodecyl glycol copolymer, Hydroxyoctacosanyl hydroxystearate, Mineral oil, Phenoxyethanol & Parabens, Magnesium sulfate heptahydrate, Dimethicone, Allantoin.
(C): Placebo comprising Water, Octyl stearate, Coco glycerides, Propylene glycol, Methoxy-PEG-22/Dodecyl glycol copolymer, PEG-22/Dodecyl glycol copolymer, Hydroxyoctacosanyl hydroxystearate, Mineral oil, Phenoxyethanol & Parabens, Magnesium sulfate heptahydrate, Dimethicone, Allantoin.

L*a*b* values compared with nonirradiated skin following repeated UVAB irradiation (3×weekly) and in the case of the application of compositions (A) and (B).

|  | Lightness L* | | | Red component a* | | | Yellow component b* | | |
| --- | --- | --- | --- | --- | --- | --- | --- | --- | --- |
|  | Number of irradiations | | | | | | | | |
| Preparation | 3 | 6 | 9 | 3 | 6 | 9 | 3 | 6 | 9 |
| Placebo | −5.32 | −12.01 | −14.01 | 4.90 | 2.33 | 0.52 | 3.09 | 6.82 | 7.93 |
| (B) | −1.05 | −5.23 | −7.13 | 0.45 | 0.77 | −0.03 | 1.11 | 2.63 | 3.49 |
| (A) | 2.18 | 8.26 | 11.40 | 0.24 | 0.45 | 0.39 | −0.38 | −0.69 | −0.21 |
| Irradiated untreated | −5.19 | −12.38 | −14.55 | 5.13 | 1.77 | −0.19 | 2.64 | 6.39 | 7.44 |

Discussion of the Results
Lightness
While the placebotreated and the untreated irradiated areas decrease in lightness to roughly the same extent, i.e. become darker, this effect is considerably less in the case of the application of the composition (B) over the time. In the case of the application of composition (A), lightening of the skin is found.
Reddening
The red component of the irradiated skin is most intense after 3 irradiations and drops back to the normal value by the end of the irradiations. The increase in the red component corresponds to the development of a UV-induced erythema, which arises only to a low degree in the case of the application of compositions (A) or (B).
Yellow Component
The yellow component increases both in the case of the application of placebo and in the untreated irradiated control area. The increase is much less in the case of the application of composition (B) and is prevented in the case of the application of composition (A).

What is claimed is:
1. A method for preventing tanning and for lightening human skin and hair which comprises applying to the hair and skin a mixture of at least two micronized organic UV filters.
2. A method according to claim 1, wherein the mixtures of organic UV filters are chosen from at least 2 classes of organic UV filters selected from the group consisting of: triazine or benzotriazole derivatives, amides containing a vinyl group, cinnamic acid derivatives, sulfonated benzimidazoles, Fischer base derivatives, diphenylmalonitriles, oxalylamides, camphor derivatives, diphenylacrylates, paraaminobenzoic acid (PABA) and derivatives thereof, salicylates and benzophenones.

3. A method according to claim 1, wherein the organic UV filters are chosen from triazine derivatives of the formula

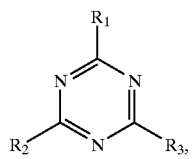
(1)

in which

R₁, R₂ and R₃, independently of one another, are hydrogen; OH; $C_1$–$C_{10}$alkoxy; —NH₂; —NH—R₄; —N(R₄)₂; —OR₄, R₄ is $C_1$–$C_5$alkyl; phenyl; phenoxy; anilino; pyrrolo, wherein phenyl, phenoxy, anilino or pyrrolo may be unsubstituted or substituted by one, two or three OH groups, carboxyl, —CO—NH₂, $C_1$–$C_5$alkyl or $C_1$–$C_5$alkoxy; a methylidenecamphor group; a group of the formula —(CH=CH)$_m$C(=O)—OR₄; a group of the formula

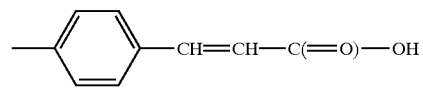

or the corresponding alkali metal, ammonium, mono-, di- or tri-$C_1$–$C_4$alkylammonium, mono-, di- or tri-$C_2$–$C_4$alkanolammonium salts, or $C_1$–$C_3$alkyl esters thereof; or a radical of the formula (1a)

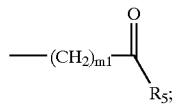
(1a)

R₅ is hydrogen; unsubstituted $C_1$–$C_5$alkyl or $C_1$–$C_5$alkyl substituted by one or more OH groups; $C_1$–$C_5$alkoxy; amino; mono- or di-$C_1$–$C_5$alkylamino; M; a radical of the formula (1b)

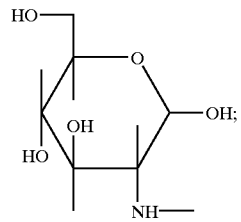

(1c)

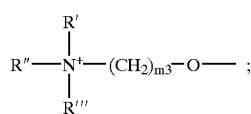

(1d)

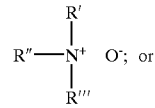

(1e)

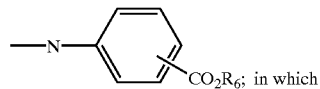

in which

R', R" and R''', independently of one another, are unsubstituted $C_1$–$C_{14}$alkyl or $C_1$–$C_{14}$alkyl substituted by one or more OH groups;

R₆ is hydrogen; M; $C_1$–$C_5$alkyl; or a radical of the formula —(CH₂)$_{m_2}$—O—T₁;

M is a metal cation;

T₁ is hydrogen; or $C_1$–$C_8$alkyl;

m is 0 or 1 m₂ is 1 to 4; and m₃ is 2 to 14.

4. A method according to claim 1, wherein the organic UV filters are chosen from triazine derivatives of the formula

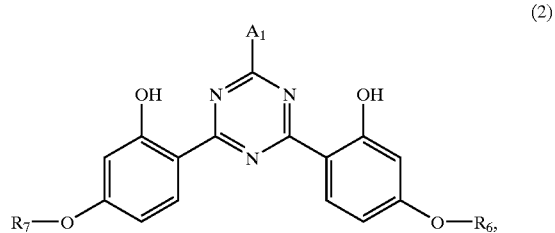
(2)

in which

R₇ and R₈, independently of one another, are $C_1$–$C_{18}$alkyl; $C_2$–$C_{18}$alkenyl; a radical of the formula —CH₂—CH(—OH)—CH₂—O—T₁; or R₇ and R₈ are a radical of the formula (2a)

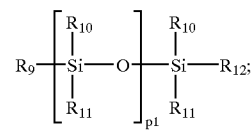
(2a)

R₉ is the direct bond; a straight-chain or branched $C_1$–$C_4$alkylene radical or a radical of the formula —$C_{m_1}H_{2m_1}$—O—;

R₁₀, R₁₁ and R₁₂, independently of one another, are $C_1$–$C_{18}$alkyl; $C_1$–$C_{18}$alkoxy or a radical of the formula

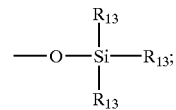

R₁₃ is $C_1$–$C_5$alkyl;

m₁ is 1 to 4;

p₁ is 0 to 5;

A₁ is a radical of the formula

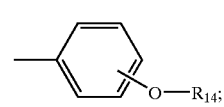
(2b)

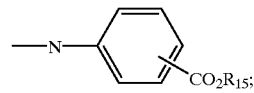
(2c)

or of the formula

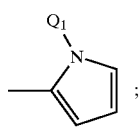
(2d)

$R_{14}$ is hydrogen; $C_1$–$C_{10}$alkyl, —$(CH_2CHR_{16}$—$O)_{n_1}$—$R_{15}$; or a radical of the formula —$CH_2$—$CH(—OH)$—$CH_2$—$O$—$T_1$;

$R_{15}$ is hydrogen; M; $C_1$–$C_5$alkyl; or a radical of the formula —$(CH_2)_{m_2}$—$O$—$(CH_2)_{m_3}$—$T_1$;

$R_{16}$ is hydrogen; or methyl;

$T_1$ is hydrogen; or $C_1$–$C_8$alkyl;

$Q_1$ is $C_1$–$C_{18}$alkyl;

M is a metal cation;

$m_2$ and $m_3$, independently of one another, are 1 to 4; and $n_1$ is 1 to 16.

5. A method according to claim 1, wherein the organic UV filters are chosen from triazine derivatives of the formula

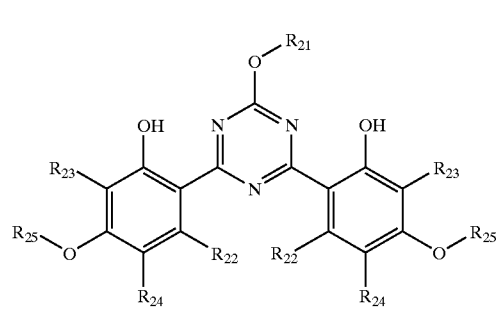
(3)

in which $R_{21}$ is $C_1$–$C_{30}$alkyl; $C_2$–$C_3$alkenyl; unsubstituted $C_5$–$C_{12}$cycloalkyl or $C_5$–$C_{12}$cycloalkyl mono- or polysubstituted by $C_1$–$C_5$alkyl; $C_1$–$C_5$alkoxy-$C_1$–$C_{12}$alkyl; amino-$C_1$–$C_{12}$alkyl; $C_1$–$C_5$monoalkylamino-$C_1$–$C_{12}$alkyl; $C_1$–$C_5$dialkylamino-$C_1$–$C_{12}$alkyl; a radical of the formula (34a)

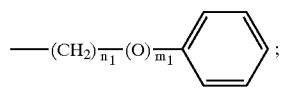

or (3b)

in which $R_{22}$, $R_{23}$ and $R_{24}$, independently of one another, are hydrogen, —OH; $C_1$–$C_{30}$alkyl, $C_2$–$C_{30}$alkenyl, $R_{25}$ is hydrogen; or $C_1$–$C_5$alkyl;

$m_1$ is 0 or 1; and $n_1$ is 1 to 5.

6. A method according to claim 1, wherein the organic UV filters are chosen from triazine derivatives of the formula

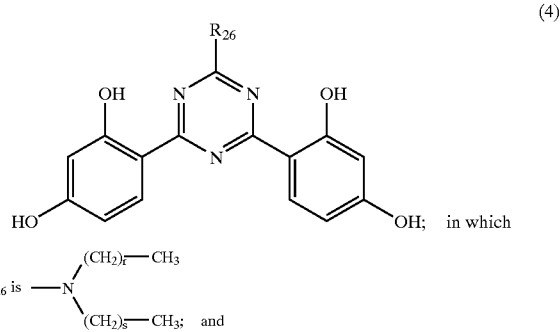
(4)

in which $R_{26}$ is r and s, independently of one another, are 0 to 20.

7. A method according to claim 1, wherein the organic UV filters are chosen from triazine derivatives of the formula

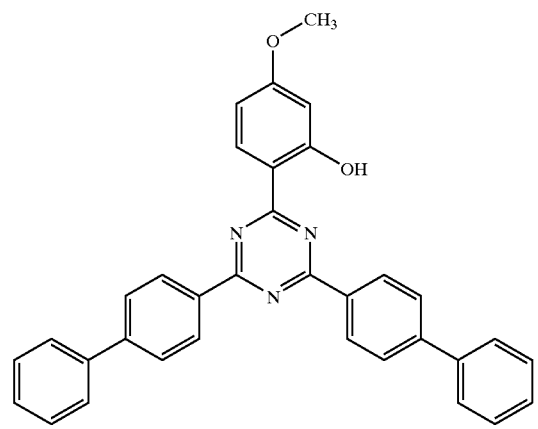
(20a)

8. A method according to claim 1, wherein the organic UV filters are chosen from triazine derivatives of the formula

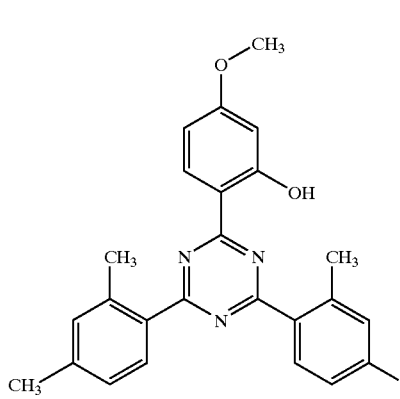
(24a)

9. A method according to claim 1, wherein the organic UV filters are chosen from triazine derivatives of the formula

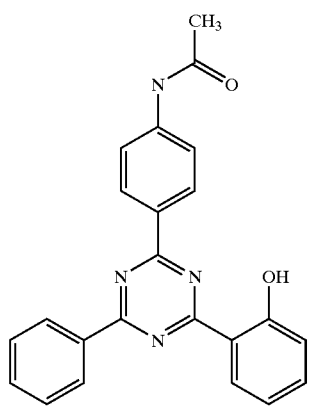

(24b)

10. A method according to claim 1, wherein the organic UV filters are chosen from triazine derivatives of the formula

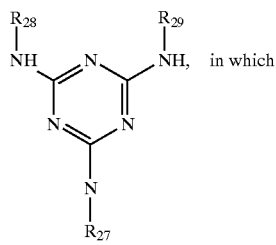

(25)

$R_{27}$, $R_{28}$ and $R_{29}$, independently of one another, are a radical of the formula

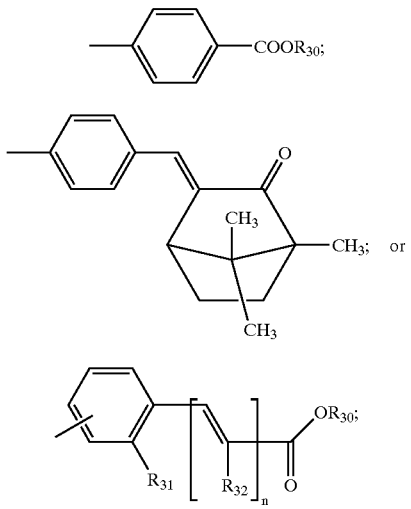

(25a)

(25b)

(25c)

$R_{30}$ is hydrogen; alkali metal; an ammonium group —N(R$_{33}$)$_4$, $R_{33}$ is hydrogen; $C_1$–$C_5$alkyl; or a polyoxyethylene radical which has 1 to 10 ethylene oxide units and the terminal OH group can be etherified with a $C_1$–$C_5$alcohol;

$R_{31}$ is hydrogen; —OH; or $C_1$–$C_6$alkoxy;

$R_{32}$ is hydrogen or —COOR$_{30}$; and n is 0 or 1.

11. A method according to claim 1, wherein the organic UV filters are chosen from benzotriazole derivatives of the formula (26)

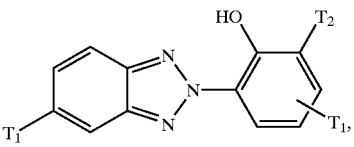

in which $T_1$ is $C_1$–$C_5$alkyl or hydrogen; and $T_2$ is $C_1$–$C_5$alkyl or phenyl-substituted $C_1$–$C_5$alkyl.

12. A method according to claim 1, wherein the organic UV filters are chosen from benzotriazole derivatives of the formula

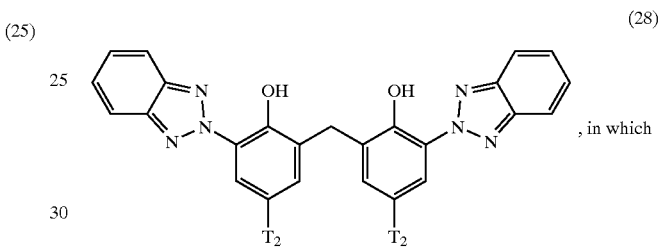

(28)

$T_2$ is $C_1$–$C_4$alkyl, isooctyl or phenyl-substituted $C_1$–$C_5$alkyl.

13. A method according to claim 1, wherein the organic UV filters are chosen from Fischer base aldehydes of the formula

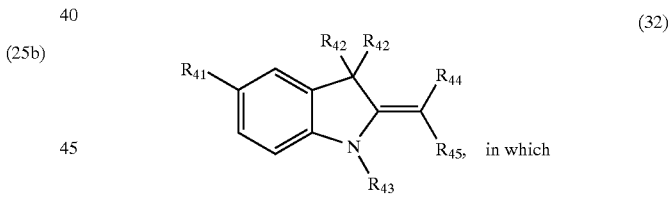

(32)

$R_{41}$ is hydrogen; $C_1$–$C_5$alkyl; $C_1$–$C_{18}$alkoxy; or halogen;

$R_{42}$ is $C_1$–$C_8$alkyl; $C_5$–$C_7$cycloalkyl; or $C_6$–$C_{10}$aryl;

$R_{43}$ is $C_1$–$C_{18}$alkyl or a radical of the formula (32a)

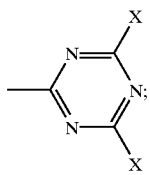

$R_{44}$ is hydrogen; or a radical of the formula

$R_{45}$ is $$-\left[N-\right]_n \begin{matrix} R_{47} & R_{48} \\ | & | \\ & C=O; \end{matrix}$$

$C_1$–$C_{18}$alkoxy; or a radical of the formula $$-CH=C-C\equiv N; \quad (32b)$$
$$\quad\quad | $$
$$\quad\quad C$$
$$\quad\; O^{\nearrow}\;\;{}^{\searrow}O-R_{49}$$

$R_{46}$ and $R_{47}$, independently of one another, are hydrogen; or $C_1$–$C_5$alkyl;

$R_{48}$ is hydrogen; $C_1$–$C_5$alkyl; $C_5$–$C_7$cycloalkyl; phenyl; phenyl-$C_1$–$C_3$alkyl;

$R_{49}$ is $C_1$–$C_{18}$alkyl;

X is Hal; a radical of the formula (32c)

$$-NH-\underset{}{\bigcirc}-CO-NH\overset{R_{46}}{\diagdown}$$

or $$HO-\underset{}{\bigcirc}-OH; \text{ and} \quad (32d)$$

14. A method according to claim 1, wherein the organic UV filters are chosen from compounds of the formula (33)

[structure with $R_{50}$, $R_{51}$, $R_{52}$, $R_{53}$, $R_{54}$, $R_{55}$, $ZO_3S$, $C_m$, $C_n$, $X_1$, $Y_1$]

in which $R_{50}$, $R_{51}$, $R_{52}$, $R_{53}$, $R_{54}$, independently of one another, are hydrogen, $C_1$–$C_8$alkyl or $C_5$–$C_{10}$cycloalkyl;

$R_{55}$ is hydrogen; $C_1$–$C_8$alkyl; $C_5$–$C_{10}$cycloalkyl; hydroxyl; $C_1$–$C_8$alkoxy; $COOR_{56}$; or $CONR_{57}R_{58}$;

$R_{56}$, $R_{57}$ and $R_{58}$, independently of one another, are hydrogen or $C_1$–$C_6$alkyl;

X and Y, independently of one another, are hydrogen, —CN; $CO_2R_{59}$; $CONR_{59}R_{60}$; or $COR_{59}$;

where the radicals X and Y may additionally be a $C_1$–$C_8$alkyl radical, a $C_5$–$C_{10}$alkyl radical or a heteroaryl radical having 5 to 6 ring atoms, where, in addition, X and Y or $R_{50}$ together with one of the radicals X and Y can represent the radical to complete a 5- to 7-membered ring which may contain up to 3 heteroatoms, where the ring atoms may be substituted by exocyclically double-bonded oxygen and/or $C_1$–$C_8$alkyl and/or $C_5$–$C_{10}$cycloalkyl radicals, and/or may contain C=C double bonds;

Z is hydrogen; ammonium; alkali metal ion; or the cation of an organic nitrogen base used to neutralize the free acid group;

$R_{59}$ and $R_{60}$, independently of one another, are hydrogen, $C_1$–$C_8$alkyl or $C_5$–$C_{10}$cycloalkyl; and n and m, independently of one another, are 0 or 1.

15. A process for the preparation of mixtures of organic UV filters according to claim 1, which comprises thoroughly mixing the UV filters present in micronized form together.

16. A process for the preparation of mixtures of organic UV filters according to claim 1, which comprises micronizing the organic UV filters as mixtures of at least two individual substances.

17. A process for the preparation of mixtures of organic UV filters according to claim 1, which comprises melting together at least two individual substances, cooling the melt, and then subjecting the resulting composite to a micronization process.

18. A composite obtained by melting together at least two organic UV filters according to claim 1.

19. A method according to claim 1, wherein an inorganic pigment is additionally mixed in.

20. A method according to claim 19, wherein the inorganic pigments are chosen from $TiO_2$, ZnO, iron oxides, mica and Ti or zinc salts of organic acids.

21. A composite obtained by melting together at least two organic UV filters according to claim 1 and at least one inorganic pigment.

22. A method according to claim 1, wherein the mixture additionally comprises an antioxidant.

23. A method according to claim 22, wherein the antioxidant is selected from the group consisting of tocopherols, ellagic acid, propyl gallate, butylated hydroxytoluene, butylated hydroxyanisole, 2,4,6-tris(3,5-di-t-butyl-4-hydroxybenzyl)mesitylene, tetrakis[methylene-3-(3',5'-di-t-butyl-4'-hydroxyphenyl)propionate]methane, the compound of the formula

[structure: bis-phenol with tert-butyl groups, CH3 groups, and acrylate ester]

[structure: benzofuranone with tert-butyl and CH3 substituents]

vanillin, ubiquinone, ferulic acid, ferulic acid derivatives, rutic acid, rutic acid derivatives; urocanic acid, urocanic acid derivatives and propolis.

24. A composite obtained by melting together at least two organic UV filters according to claim 1 and at least one antioxidant, and, optionally, one or more inorganic pigments.

25. A method according to claim 1, wherein the mixture additionally comprises a cationic or anionic compound.

26. A method according to claim 25, wherein the cationic or anionic compound is chosen from camphorbenzalkonium methosulfates, fatty amines, betaines, quats, citric monoglyceride, sodium methylcocoyltaurate, phospholipids, ceramides and phytosterols.

27. A composite obtainable by melting together at least two organic UV filters according to claim 1 and at least one cationic or anionic compound.

28. A method according to claim 1, wherein the mixture additionally comprises a pharmaceutical or cosmetic active ingredient.

29. A cosmetic formulation comprising a mixture of organic UV filters according to claim 1, optionally one or more compounds selected from the group consisting of antioxidants, inorganic pigments and cationic or anionic compounds, and cosmetically compatible carriers or auxiliaries.

30. A cosmetic formulation according to claim 29, which additionally comprises an oil-soluble, nonmicronized UV filter.

31. A pharmaceutical formulation comprising a mixture of at least two organic UV filters according to claim 1, optionally one or more compounds selected from the group consisting of antioxidants, inorganic pigments and cationic or anionic compounds, and pharmaceutically compatible carriers or auxiliaries.

* * * * *